(12) United States Patent
Tsumaki

(10) Patent No.: US 9,725,737 B2
(45) Date of Patent: Aug. 8, 2017

(54) CHONDROCYTE-LIKE CELL, AND METHOD FOR PRODUCING SAME

(71) Applicant: iPS ACADEMIA JAPAN, INC., Kyoto-shi (JP)

(72) Inventor: Noriyuki Tsumaki, Suita (JP)

(73) Assignee: IPS ACADEMIA JAPAN, INC., Kyoto-shi (JP)

( * ) Notice: Subject to any disclaimer, the term of this patent is extended or adjusted under 35 U.S.C. 154(b) by 789 days.

(21) Appl. No.: 13/926,183

(22) Filed: Jun. 25, 2013

(65) Prior Publication Data

US 2013/0287695 A1    Oct. 31, 2013

Related U.S. Application Data

(62) Division of application No. 13/140,164, filed as application No. PCT/JP2009/071184 on Dec. 18, 2009, now abandoned.

(30) Foreign Application Priority Data

Dec. 18, 2008  (JP) ................................. 2008-322754
May 15, 2009  (JP) ................................. 2009-118790

(51) Int. Cl.
| | | |
|---|---|---|
| C12N 5/00 | (2006.01) | |
| C12N 5/02 | (2006.01) | |
| C12N 15/85 | (2006.01) | |
| A61K 31/713 | (2006.01) | |
| A61L 27/38 | (2006.01) | |
| C12N 5/077 | (2010.01) | |
| A61K 35/32 | (2015.01) | |
| A61K 49/00 | (2006.01) | |
| A61K 35/12 | (2015.01) | |

(52) U.S. Cl.
CPC ............ *C12N 15/85* (2013.01); *A61K 31/713* (2013.01); *A61K 35/32* (2013.01); *A61K 49/0004* (2013.01); *A61L 27/3817* (2013.01); *A61L 27/3852* (2013.01); *C12N 5/0655* (2013.01); *A61K 35/12* (2013.01); *C12N 2501/60* (2013.01); *C12N 2510/00* (2013.01)

(58) Field of Classification Search
CPC .............. C12N 5/0696; C12N 2501/60; C12N 2510/00; C12N 5/0655; C12N 2501/602; C12N 2501/603; C12N 2501/604; C12N 2501/15

See application file for complete search history.

(56) References Cited

U.S. PATENT DOCUMENTS

| | | |
|---|---|---|
| 2009/0047263 A1 | 2/2009 | Yamanaka |
| 2009/0068742 A1 | 3/2009 | Yamanaka |
| 2009/0227032 A1 | 9/2009 | Yamanaka |
| 2010/0062533 A1 | 3/2010 | Yamanaka |
| 2010/0210014 A1 | 8/2010 | Yamanaka |
| 2010/0216236 A1 | 8/2010 | Yamanaka |

FOREIGN PATENT DOCUMENTS

| | | | |
|---|---|---|---|
| EP | 1 970 446 | 9/2008 | |
| JP | 2003-059692 A | 2/2003 | |
| JP | 2004016109 | * 1/2004 | ............. C12N 15/00 |
| JP | 2004-267052 | 9/2004 | |
| JP | 2009-292787 A1 | 12/2009 | |
| WO | 2007/069666 A1 | 6/2007 | |

OTHER PUBLICATIONS

Takahashi et al. Induction of Pluripotent Stem Cells from Adult Human Fibroblasts by Defined Factors. Cell, 2007, vol. 131, pp. 1-12.*
Solchaga et al. Chondrogenic Differentiation of Bone Marrow-Derived Mesenchymal Stem Cells: Tips and Tricks. Methods Mol Biol., 2011, vol. 698, pp. 253-278.*
Stadtfeld et al. Induced pluripotent stem cells generated without viral integration. Science, vol. 322. pp. 945-949.*
Okita et al. Generation of mouse induced pluripotent stem cells without viral vectors. Science. vol. 322, pp. 949-953.*
Gonzales et al. Generation of mouse-induced pluripotent stem cells by transient expression of a single nonviral polycistronic vector. PNAS, 2009, vol. 106, pp. 8918-8922.*
Rodriguez et al. Manipulation of OCT4 Levels in Human Embryonic Stem Cells Results in Induction of Differential Cell Types. Experimental Biology and Medicine, 2007, vol. 232, pp. 1368-1380.*
Yamanaka, S. Induction of pluripotent stem cells from mouse fibroblasts by four transcription factors. Cell Proliferation, 2008, vol. 41, pp. 51-56.*
Outani, Hidetatsu, et al., "Direct induction of Chondrogenic Cells from Human Dermal Fibroblast Culture by Defined Factors," Plos One, vol. 8, Issue 10, e77365 (2013), pp. 1-12.
R. Katayama, et al.; "Introduction of CDMP1 Gene Into Bone Marrow-Derived Mesenchymal Stem Cells and Promotion of Cartilage Differentiation Induction;" J. Jpn. Orthop. Assoc.; vol. 75; No. 8; 2001; pp. S850, 1-B-P1-4 (3 sheets total).
T. Iwai, et al.; "Role of Smad7 during endochondral bone formation;" The 20th Annual Meeting of the Japanese Society of Cartilage Metabolism; Mar. 2, 2007; p. 76.

(Continued)

*Primary Examiner* — Valarie Bertoglio
(74) *Attorney, Agent, or Firm* — Kratz, Quintos & Hanson, LLP

(57) ABSTRACT

Disclosed is a cell which enables the reproduction of a cartilage tissue and has a proliferative ability. Also disclosed is a technique for providing a cell supply source which can be used in a definitive treatment of osteochondrosis deformans. A chondrocyte-like cell which has the same properties as those of a chondrocyte and can proliferate can be produced by selecting a combination of an Myc family gene and/or a Klf family gene and a SOX9 gene and introducing the combination into a somatic cell. The chondrocyte-like cell can be used for a medical purpose of cartilage regeneration.

6 Claims, 12 Drawing Sheets

(56) References Cited

OTHER PUBLICATIONS

N. Tsumaki, Research Report (Research Project on Prevention and Treatment of Immunoallergic Disease) supported in part by Health and Labour Sciences Research Grants; Apr. 2007; pp. 8-11, cover sheet, end sheet and translation (10 sheets total).

D. Ikegami, et al.; "Sox9 is essential for maintenance of chondrocytic phenotype and chondrocyte survival;" The 22nd Annual Meeting of the Japanese Society of Cartilage Metabolism; Mar. 6, 2009; p. 78 and cover sheet (2 sheets total).

W. Hunter, "Of the Structure and Diseases of Articulating Cartilages;" Philos Trans Lond; vol. 42; 1743; pp. 514-522/p. 4 of specification.

C. Chung, et al.; "Engineering cartilage tissue;" Advanced Drug Delivery Reviews 60; 2008; pp. 243-262/p. 4 of specification.

J. Gao, et al.; "Stem cells for tissue engineering of articular cartilage;" Proc. Inst. Mech. Eng. Part H; vol. 221; No. 5; 2007; pp. 441-450/p. 4 of specification.

U.R. Goessler, et al.; "Expression of collagen and fiber-associated proteins in human septal cartilage during in vitro dedifferentiation;" Int. J. Mol. Med.; vol. 14; 2004; pp. 1015-1022/p. 4 of specification.

J. Kramer, et al.; "Embryonic stem cell-derived chondrogenic differentiation in vitro: activation by BMP-2 and BMP-4;" Mechanisms of Development; vol. 92; 2000; pp. 193-205/p. 4 of specification.

N.S. Hwang, et al.; "Effects of Three-Dimensional Culture and Growth Factors on the Chondrogenic Differentiation of Murine Embryonic Stem Cells;" Stem Cells; vol. 24; 2006; pp. 284-291/p. 4 of specification.

N.S. Hwang, et al.; "Derivation of Chondrogenically-Committed Cells from Human Embryonic Cells for Cartilage Tissue Regeneration;" PLoS One; vol. 3; Issue 6; Jun. 2008; e2498; pp. 1-10/p. 4 of specification.

V. Vacanti, et al.; "Phenotypic Changes of Adult Porcine Mesenchymal Stem Cells Induced by Prolonged Passaging in Culture;" Journal of Cellular Physiology; vol. 205; No. 2; 2005; pp. 194-201/p. 4 of specification.

A. Nagai, et al.; "Multilineage Potential of Stable Human Mesenchymal Stem Cell Line Derived from Fetal Marrow;" PLoS One; Issue 12; Dec. 2007; p. e1272; pp. 1-18/p. 4 of specification.

M. Amit, et al.; "Derivation and spontaneous differentiation of human embryonic stem cells;" J. of Anat.; vol. 200; 2002; pp. 225-232/p. 4 of specification.

E.J. Koay, et al.; "Tissue Engineering with Chondrogenically Differentiated Human Embryonic Stem Cells;" Stem Cells; vol. 25; No. 9; 2007; pp. 2183-2190/p. 4 of specification.

S. Wakitani, et al.; "Embryonic stem cells injected into the mouse knee joint form teratomas and subsequently destroy the joint;" Rheumatology; vol. 42; 2003; pp. 162-165/p. 4 of specification.

T. Aoi, et al.; "Generation of Pluripotent Stem Cells from Adult Mouse Liver and Stomach Cells;" Science; vol. 321 (5889) Aug. 1, 2008; pp. 699-702/p. 4 of specification.

M. Nakagawa, et al.; "Generation of induced pluripotent stem cells without Myc from mouse and human fibroblasts;" Nature Biotechnology; vol. 26; No. 1; Jan. 2008; pp. 101-106/p. 4 of specification.

K. Takahashi, et al.; "Induction of pluripotent stem cells from fibroblast cultures;" Nature Protocols; vol. 2; No. 12; 2007; pp. 3081-3089/p. 4 of specification.

K. Takahashi, et al.; "Induction of Pluripotent Stem Cells from Adult Human Fibroblasts by Defined Factors;" Cell;vol. 131; No. 5; Nov. 30, 2007; pp. 861-872/p. 4 of specification.

K. Takahashi, et al.; "Induction of Pluripotent Stem Cells from Mouse Embryonic and Adult Fibroblast Cultures by Defined Factors;" Cell; vol. 126; No. 4; Aug. 25, 2006; pp. 663-676/p. 5 of specification.

K. Okita, et al.; "Generation of germline-competent induced pluripotent stem cells;" Nature; vol. 448 (7151); 2007; pp. 313-317/p. 5 of specification.

M. Wernig, et al.; "In vitro reprogramming of fibroblasts into a pluripotent ES-cell-like state;" Nature; vol. 448 (7151) 2007; pp. 318-324/p. 5 of specification.

N. Maherali, et al.; "Directly Reprogrammed Fibroblasts Show Global Epigenetic Remodeling and Widespread Tissue Contribution;" Cell Stem Cell; vol. 1; Jul. 2007; pp. 55-70/p. 5 of specification.

A. Meissner, et al.; "Direct reprogramming of generically unmodified fibroblasts into pluripotent stem cells;" Nature Biotechnology; vol. 25; No. 10; Oct. 2007; pp. 1177-1181/p. 5 of specification.

M. Wernig, et al.; "c-Myc is Dispensable for Direct Reprogramming of Mouse Fibroblasts;" Cell Stem Cell 2; Jan. 2008; pp. 10-12/p. 5 of specification.

J. Yu, et al.; "Induced Pluripotent Stem Cell Lines Derived from Human Somatic Cells;" Science; vol. 318 (5858); 2007; pp. 1917-1920/p. 5 of specification.

I.H. Park, et al.; "Reprogramming of human somatic cells to pluripotency with defined factors;" Nature; vol. 451; (7145); Jan. 10, 2008; pp. 141-146/p. 5 of specification.

Tew, et al., "Retroviral transduction with SOX9 enhances re-expression of the chondrocyte phenotype in passaged osteoarthritic human articular chondrocytes," Osteoarthritis and Cartilage, Jan. 1, 2005, vol. 13, No. 1, pp. 80-89.

Haruhiko Akiyama, "Control of chondrogenesis by the transcription facto Sox9," Modern Rheumatology; Official Journal of the Japan college of Pheumatology, Mar. 20, 2008, vol. 18, No. 3, pp. 213-219.

Outani, et al., "Induction of chndrogenic cells from dermal fibroblast culture by defined factors does not involve a pluripotent state," Biochemical and Biophysical Research Communications, Aug. 1, 2011, vol. 441, No. 3, pp. 607-612.

Kunihiko Hiramatsu et al.: "Generation of hyaline cartilaginous tissue from mouse adult dermal fibroblast culture by defined factors", The Journal of Clinical Investigation, Technical Advance, Feb. 2011, pp. 1-18.

Michael H. Ross et al.: "Histology a Text and Atlas with Correlated Cell and Molecular Biology", Sixth Edition, Wolters Kluwer/Lippincott Williams & Wilkins (2011) (6 pages).

Nicolai Miosge et al.: "Expression of collagen type I and type II in consecutive stages of human osteoarthritis", Histochem Cell Biol (2004), 122, pp. 229-236.

Asheesh Bedi et al.: "Management of Articular Cartilage Defects of the Knee", The Journal of Bone and Joint Surgery Inc., 2010, 92, pp. 994-1009.

Lawrence Rosenberg: "Chemical Basis for the Histological Use of Safranin O in the Study of Articular Cartilage", The Journal of Bone and Joint Surgery Inc., 1971, 53-A, No. 1, pp. 69-82.

Chen et al.: "Technology Insight: adult stem cells in cartilage regeneration and tissue engineering", Abstract of Nat Clin Pract Rheumatol, Jul. 2006, 2(7) 373-382, Pubmed ID 16932723.

Nakayama, Naoki et al., "Macroscopic cartilage formation with embryonic stem-cell-derived mesodermal progenitor cells", Journal of Cell Science, vol. 116, No. 10, May 15, 2003, pp. 2015-2028.

Hiramatsu, Kunihiko et al., "Generation of Hyaline cartilaginous tissue from mouse adult dermal fibroblast culture by defined factors", Journal of Clinical Investigation, vol. 121, No. 2, Feb. 2011, pp. 640-657 (Reprinted pp. 1-18).

Ross, Michael H. et al., "Histology", 2011, Wolters Kluwers, pp. 204-217 (pp. 208, 209, 212-215 are missing).

Chen, Faye H. et al., "Technology Insight: adult stem cells in cartilage regeneration and tissue engineering", Database accession No. NLM16932723 (Abstract).

Ikeda, Toshiyuki et al., "The Combination of SOX5, SOX6, and SOX9 (the SOX Trio) Provides Signals Sufficient for Induction of Permanent Cartilage", Arthritis and Rheumatism, vol. 50, No. 11, Nov. 2004, pp. 3561-3573.

Examination Report dated Jun. 28, 2012, in counterpart European Patent Application No. 09833512.8.

Oldershaw, Rachel A., et al., "Directed differentiation of human embryonic stem cells toward chondrocytes", Nature Biotechnology, vol. 28, No. 11, Nov. 2010, published online Oct. 22, 2010, doi:10.1038/nbt.1683, pp. 1187-1194 plus 14-page online appendix.

Arvind Shakya, et al., "Pluripotency Transcription Factor Oct4 Mediates Stepwise Nucleosome Demethylation and Depletion", Molecular and Cellular Biology, Mar. 2015, vol. 35, No. 6, pp. 1014-1025.

(56) References Cited

OTHER PUBLICATIONS

Ulf Tiemann, et al., "Counteracting Activities of Oct4 and KLF4 during Reprogramming to Pluripotency", Stem Cell Reports, Mar. 11, 2014, vol. 2, pp. 351-365.
Xia Wang, et al., "Concise Review: Isoforms of OCT4 Contribute to the Confusing Diversity in Stem Cell Biology", Stem Cells, 2010, 28, pp. 885-893.
Guilai Shi, et al., "Role of Oct 4 in maintaining and regaining stem cell pluripotency", Stem Cell Research & Therapy, 2010, 1:39, 9 pages.

* cited by examiner

A

B

C

A MK-7, 16 weeks x 100 x 200

B MK-10, 8 weeks x 40 x 200

CHONDROCYTE-LIKE CELL, AND METHOD FOR PRODUCING SAME

TECHNICAL FIELD

The present invention relates to chondrocyte-like cells that are induced from somatic cells and have proliferative capabilities and the properties of the chondrocytes, and to processes for producing the chondrocyte-like cells. The invention also concerns cell preparations for cartilage tissue regeneration, implants, implant producing processes, cartilage disease therapeutic methods, and drug efficacy determining methods for determining the efficacy of a tested substance for cartilage disease, all using the chondrocyte-like cells. The invention also relates to chondrocyte-like cell preparation compositions used to induce somatic cells to the chondrocyte-like cells.

BACKGROUND ART

Articular cartilage has a role as a joint lubricant for absorbing impact at the diarthrodial joints during articular movement. The mechanical functions of the cartilage are imparted by the cartilage extracellular matrix constructed from type II and type XI collagens, and collagenous fibrils such as proteoglycan. It is known that the cartilage extracellular matrix is produced by the chondrocytes intrinsic to the cartilage.

Osteoarthritis is a typical cartilage tissue disease, caused by the aggravation of wear, damage, and degeneration of the articular cartilage in response to mechanical stresses (such as repetitive loading, excessive exercise, and trauma) and aging. The symptoms of osteoarthritis include joint pain during joint movement (movement pain) and a restricted range of motion (restricted motion), which lower the quality of daily life. In Japan, osteoarthritis affects about 20% of the population over the age 50, and is expected to affect more people as the medical development and improved lifestyle are expected to raise the average life expectancy. Osteoarthritis thus poses a big challenge in the aging society.

Conventional osteoarthritis therapies employ resting to prevent aggravation of symptoms or controlling pain by, for example, the administration of antiphlogistic analgetics or supplements, or the intraarticular administration of joint lubricants. These methods, however, are only supportive, and do not represent a definitive therapy, because the chondrocytes have only weak repairing capabilities (see Non-Patent Literature 1), and cannot regenerate cartilage tissue. A procedure using a metallic artificial replacement joint has been practiced for osteoarthritis cases with progressive cartilage degeneration. However, artificial joints have a number of drawbacks, including a heavy burden put on patients during the procedure, deterioration due to wear, a tendency to dislocate, and possible revision surgery necessitated by a loosened artificial joint.

Recently, a technique that enables a definitive treatment of osteochondrosis deformans through cartilage tissue regeneration has caught attention for the treatment of osteochondrosis deformans which does not respond well to conventional therapies. For such a technique to be realized, development of an easy-to-obtain cell supply source that can produce large numbers of cells while retaining the capability to differentiate and form cartilage tissue is urgently needed (see Non-Patent Literatures 2 and 3). Chondrocytes are considered as a good candidate for such a cell supply source used for cartilage tissue regeneration. However, because chondrocytes are limited in number and cause dedifferentiation through monolayer expansion (see Non-Patent Literature 4), recent studies focus more on the development of a technique that induces formation of cartilage tissue with the use of bone marrow-derived mesenchymal stem (MS) cells or embryonic stem (ES) cells (see Non-Patent Literatures 5 to 7). However, MS cells have only limited proliferative capabilities, and recent studies suggest that the cartilage produced from MS cells is unstable, and lacks sufficient cartilage properties (see Non-Patent Literatures 8 and 9). With regard to ES cell-derived differentiated cells, there are concerns that the cells, as an inhomogeneous population, may fail to provide sufficient cartilage tissue functions (see Non-Patent Literatures 10 and 11), or may cause formation of teratoid tumors (see Non-Patent Literature 12).

There are also reports of a technique that has brought innovation in the field of regenerative medicine, specifically a technique that reprograms and induces somatic cells to induced pluripotent stem (iPS) cells by introducing Oct3/4, Klf4, c-Myc, and Sox2 coding genes into the somatic cells (see Patent Literature 1, Non-Patent Literatures 13 to 24). However, because of the pluripotency of iPS cells, use of iPS cells for cartilage tissue regeneration requires the establishment of a technique that enables the cells to differentiate into a homogeneous chondrocyte population, and there are still technical problems that need to be solved for practical applications in cartilage tissue regeneration.

Over these backgrounds, there is a growing need for the development of cells that can be directly induced to only chondrocytes, and that have cartilage tissue regenerative capabilities and a proliferative ability, and for a cell supply source that can also be used for a definitive treatment of osteochondrosis deformans.

CITATION LIST

Patent Literature

PTL 1: International Publication 2007/069666

Non-Patent Literature

NPL 1: W. Hunter, Philos Trans Lond 42, 514 (1743).
NPL 2: C. Chung and J. A. Burdick, Adv Drug Deliv Rev 60 (2), 243 (2008).
NPL 3: J. Gao, J. Q. Yao, and A. I. Caplan, Proc. Inst. Mech. Eng. [H]. 221 (5), 441 (2007).
NPL 4: U. R. Goessler, P. Bugert, K. Bieback et al., Int. J. Mol. Med. 14 (6), 1015 (2004).
NPL 5: J. Kramer, C. Hegert, K. Guan et al., Mech. Dev. 92 (2), 193 (2000).
NPL 6: N. S. Hwang, M. S. Kim, S. Sampattavanich et al., Stem Cells 24 (2), 284 (2006).
NPL 7: N. S. Hwang, S. Varghese, and J. Elisseeff, PLoS ONE 3 (6), e2498 (2008).
NPL 8: V. Vacanti, E. Kong, G. Suzuki et al., J. Cell. Physiol. 205(2), 194 (2005).
NPL 9: A. Nagai, W. K. Kim, H. J. Lee et al., PLoS ONE 2 (12), e1272 (2007).
NPL 10: M. Amit and J. Itskovitz-Eldor, Journal of anatomy 200 (Pt3), 225 (2002).
NPL 11: E. J. Koay, G. M. Hoben, and K. A. Athanasiou, Stem Cells 25 (9), 2183 (2007).
NPL 12: S. Wakitani, K. Takaoka, T. Hattori et al., Rheumatology (Oxford). 42 (1), 162 (2003).
NPL 13: T. Aoi, K. Yae, M. Nakagawa et al., Science 321 (5889), 699 (2008).

NPL 14: M. Nakagawa, M. Koyanagi, K. Tanabe et al., Nat. Biotechnol. 26 (1), 101 (2008).
NPL 15: K. Takahashi, K. Okita, M. Nakagawa et al., Nature protocols 2 (12), 3081 (2007).
NPL 16: K. Takahashi, K. Tanabe, M. Ohnuki et al., Cell 131 (5), 861 (2007).
NPL 17: K. Takahashi and S. Yamanaka, Cell 126 (4), 663 (2006).
NPL 18: K. Okita, T. Ichisaka, and S. Yamanaka, Nature 448 (7151), 313 (2007).
NPL 19: M. Wernig, A. Meissner, R. Foreman et al., Nature 448 (7151), 318 (2007).
NPL 20: N. Maherali, R. Sridharan, W. Xie et al., Cell stem cell 1(1), 55 (2007).
NPL 21: A. Meissner, M. Wernig, and R. Jaenisch, Nat. Biotechnol. (10), 1177 (2007).
NPL 22: M. Wernig, A. Meissner, J. P. Cassady et al., Cell stem cell 2 (1), 10 (2008).
NPL 23: J. Yu, M. A. Vodyanik, K. Smuga-Otto et al., Science 318 (5858), 1917 (2007).
NPL 24: I. H. Park, R. Zhao, J. A. West et al., Nature 451 (7175), 141 (2008).

SUMMARY OF INVENTION

Technical Problem

It is an object of the present invention to solve the foregoing technical problems. Specifically, an object of the present invention is to establish a technique for developing cells that have cartilage tissue regenerative capabilities and a proliferative ability, and for providing a cell supply source that can also be used for a definitive treatment of osteochondrosis deformans.

Solution to Problem

The present inventors conducted intensive studies to solve the foregoing problems, and found that chondrocyte-like cells that have a proliferative ability and the properties of the chondrocytes could be produced by introducing into somatic cells a combination of Myc family gene and/or Klf family gene and SOX9 gene selected from large numbers of differentiating cell reprogramming factors and cartilage-associated genes. It was confirmed that the chondrocyte-like cells actually obtained were able to proliferate in a monolayer culture, and expressed cartilage specific markers. It was also confirmed that the chondrocyte-like cells were able to form a cartilage tissue when cultured using a collagen gel as a scaffold, or when administered to an organism without using a scaffold. The present invention was completed based on these findings upon further studies.

Specifically, the present invention provides the following aspects of invention.
Item 1.
A chondrocyte-like cell producing process including the step of introducing into a somatic cell a SOX9 gene and at least one gene selected from the group consisting of Myc family gene and Klf family gene.
Item 2.
A producing process according to Item 1, wherein the Myc family gene is a c-Myc gene.
Item 3.
A producing process according to Item 1 or 2, wherein the Klf family gene is a Klf4 gene.
Item 4.
A producing process according to any one of Items 1 to 3, wherein the somatic cell originates in humans.
Item 5.
A producing process according to Item 1 or 2, wherein the somatic cell is a dermal fibroblast or an adipose tissue-derived stromal cell.
Item 6.
A chondrocyte-like cell obtained by introducing into a somatic cell a SOX9 gene and at least one gene selected from the group consisting of Myc family gene and Klf family gene.
Item 7.
A chondrocyte-like cell according to Item 6, wherein the Myc family gene is a c-Myc gene.
Item 8.
A chondrocyte-like cell according to Item 6 or 7, wherein the Klf family gene is a Klf4 gene.
Item 9.
A chondrocyte-like cell according to any one of Items 6 to 8, wherein the somatic cell originates in humans.
Item 10.
A chondrocyte-like cell according to any one of Items 6 to 9, wherein the somatic cell is a dermal fibroblast or an adipose tissue-derived stromal cell.
Item 11.
A cell preparation for cartilage tissue regeneration, including the chondrocyte-like cell of any one of Items 6 to 9.
Item 12.
A cell preparation according to Item 11, wherein the cell preparation includes a scaffolding material.
Item 13.
A cell preparation according to Item 12, wherein the scaffolding material is a collagen.
Item 14.
An implant including a cartilage tissue constructed by using the chondrocyte-like cell of any one of Items 6 to 8.
Item 15.
A process for producing a cartilage tissue implant,
the process including the steps of:
administering the chondrocyte-like cell of any one of Items 6 to 8 into a body of a mammal; and
removing a cartilage tissue formed from the chondrocyte-like cell in the body of the mammal.
Item 16.
A cartilage disease therapeutic method,
the method including the steps of:
administering the chondrocyte-like cell of any one of Items 6 to 8 into a cartilage disease patient at a non-cartilage tissue site; and
removing a cartilage tissue formed from the chondrocyte-like cell, and transplanting the removed cartilage tissue to the cartilage disease site of the patient.
Item 17.
A use of the chondrocyte-like cell of any one of Items 6 to 9 for the production of a cell preparation for cartilage tissue regeneration.
Item 18.
A use according to Item 17, wherein the cell preparation for cartilage tissue regeneration is a therapeutic agent for cartilage disease.
Item 19.
A use of a composition containing the chondrocyte-like cell of any one of Items 6 to 9 and a scaffolding material for the production of a cell preparation for cartilage tissue regeneration.

Item 20.

A use according to Item 19, wherein the scaffolding material is a collagen.

Item 21.

A non-human mammal forming a cartilage tissue, wherein the non-human mammal is produced by administering the chondrocyte-like cell of any one of Items 6 to 9 into a non-human mammal, and by forming a cartilage tissue from the chondrocyte-like cell in a body of the mammal.

Item 22.

A method for determining the efficacy of a tested substance for a cartilage tissue, the method including the step of administering the tested substance to the non-human mammal of Item 21 and determining the efficacy of the tested substance for the cartilage tissue.

Item 23.

A chondrocyte-like cell preparation composition, including a SOX9 gene and at least one gene selected from the group consisting of Myc family gene and Klf family gene.

Item 24.

A chondrocyte-like cell preparation composition according to Item 23, wherein a SOX9 gene and at least one gene selected from the group consisting of Myc family gene and Klf family gene are contained in a form introducible to a somatic cell.

Advantageous Effects of Invention

The present invention provides chondrocyte-like cells that have a proliferative ability and the properties of the chondrocytes, and thus can provide a medical means effective for the treatment of cartilage disease that involve cartilage damage such as in osteochondrosis deformans. Further, the present invention enables production of chondrocyte-like cells from the somatic cells of patients suffering from osteoarthritis and a wide range of other cartilage diseases including a growth cartilage disease such as chondrodystrophy, and can thus contribute to elucidating the pathology of the disease by performing various analyses. The chondrocyte-like cells produced from humans are particularly suitable as material for the discovery and development of drugs.

Further, because the present invention can be used to obtain chondrocyte-like cells from skin tissue-derived somatic cells such as skin fibroblasts and subcutaneous adipose tissue-derived stromal cells, the invention is highly useful in the clinic from the standpoint of reducing burdens on patients and cell donors.

DESCRIPTION OF EMBODIMENTS

Figure 1:
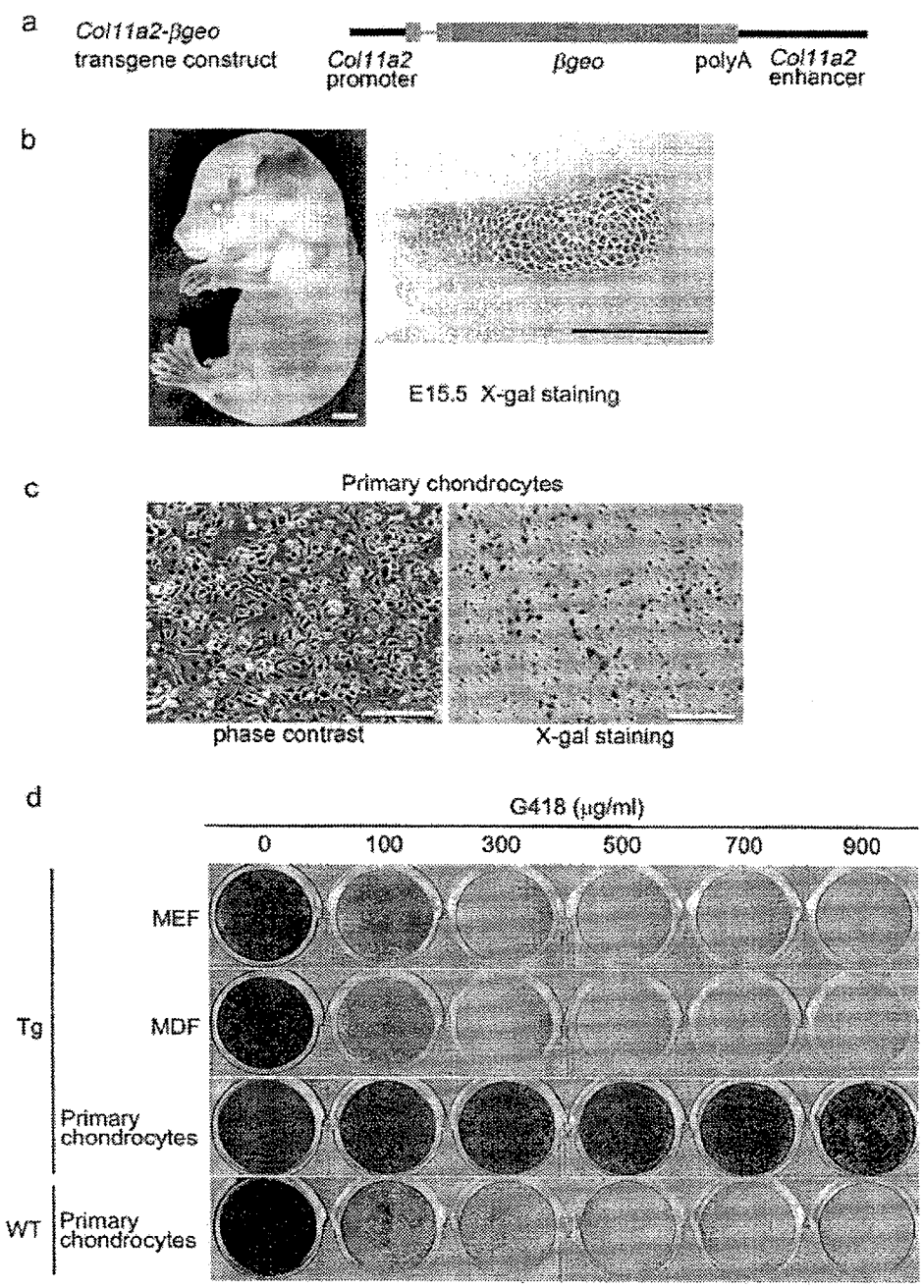
FIG. 1 is a diagram representing a Col11a2-β geo transgenic mouse, and the results of evaluations on the properties of the primary chondrocytes, MEFs, and MDFs isolated from the mouse; a, a configuration of a gene introduced into the transgenic mouse; b (left), an image of a Col11a2-β geo transgenic mouse stained with X-gal; b (right), the tissue analysis result for the cartilage of the X-gal-stained Col11a2-β geo transgenic mouse; c (left), the primary chondrocytes prepared from the β geo transgenic mouse, observed under a phase-contrast microscope; c (right), the result of the X-gal staining of the primary chondrocytes prepared from the β geo transgenic mouse; d, the results of incubating the primary chondrocytes, MEFs, and MDFs prepared from the β geo transgenic mouse, and the primary chondrocytes prepared from wild-type F1 hybrid mouse in the presence of 0 to 900 μg/ml G418, in which "Tg" means cells of β geo transgenic mouse origin, and "WT" means cells of wild-type littermate mouse origin; the same denotation is also used in the other figures in the same meaning.

1. Chondrocyte-Like Cell Producing Process, and Use of Chondrocyte-Like Cells

As used herein, "chondrocyte-like cells" means cells that have a proliferative ability and the properties of the chondrocytes, with the capabilities to form or regenerate cartilage tissue (in other words, cartilage stem cells). Herein, "having the properties of the chondrocytes" means showing positive with the specific staining for chondrocytes and expressing chondrocyte marker genes.

A chondrocyte-like cell producing process of the present invention is a process that includes the step of introducing into somatic cells at least one gene selected from the group consisting of Myc family gene and Klf family gene, together with SOX9 gene. The producing process of the present invention is described below.

In the present invention, the type of somatic cells induced to chondrocyte-like cells is not particularly limited, and those originating in any tissue or site can be used. Examples of somatic cells usable in the present invention include tissue-derived-cells such as those from the skin, subcutaneous adipose, muscle, placenta, bone, and cartilage. More specific examples include dermal fibroblasts, subcutaneous adipose tissue-derived stromal cells (subcutaneous adipose cells), embryonic fibroblasts, adipose cells, muscle cells, osteoblasts, and chondrocytes. Of these, skin-derived cells and subcutaneous adipose cells are preferred, and skin fibroblasts and subcutaneous adipose tissue-derived stromal cells are particularly preferred, because these cells are only mildly invasive to organism, and can more efficiently produce chondrocyte-like cells. Material can be selected from these various types of cells, and the fact that readily available cells such as skin-derived cells and subcutaneous adipose tissue-derived cells can be used is particularly advantageous in clinical settings from the standpoint of reducing the burden on patients and providing a stable cell supply. Further, the somatic cells may be commercially available products, or somatic cells differentiated from cells such as ES cells or mesenchymal stem cells.

Further, the somatic cells may be appropriately selected from cells that originate in mammals such as humans, mice, rats, hamsters, rabbits, cats, dogs, sheep, pigs, cows, goats, and monkeys, depending on the intended use of the chondrocyte-like cells, and cells originating in humans are preferred for therapeutic purposes in humans. The human-derived somatic cells may originate in any of fetuses, infants, children, and adults. When the chondrocyte-like cells are used for therapeutic purposes in humans, it is desirable to use somatic cells collected from a patient.

In the present invention, the somatic cells are induced to chondrocyte-like cells by introducing into the somatic cells at least one gene selected as a reprogramming factor from the group consisting of Myc family gene and Klf family gene, in combination with the cartilage-inducible transcription factor SOX9 gene.

Examples of Myc family gene include c-Myc, N-Myc, and L-Myc. The Myc family genes may be used either alone or in combinations of two or more. Among these Myc family genes, the present invention preferably uses c-Myc gene and L-Myc gene, more preferably c-Myc gene. c-Myc gene is known as a transcriptional regulator involved in cell differentiation and proliferation (S. Adhikary, M. Elilers, Nat.

Ray. Mol. Cell. Biol., 6, pp 635-645, 2005), and has known base sequences (NCBI accession Number NM_010849 (human), NM_002467 (Mouse)). N-Myc gene and L-Myc gene also have known base sequences (NCBI accession Number NM_005378 (human), NM_008709 (Mouse)), and (NCBI accession Number NM_005376 (human), NM_008506 (Mouse)), respectively. Note that NCBI in this specification is the abbreviation for National Center for Biotechnology Information.

Examples of Klf family gene include Klf1, Klf2, Klf4, and Klf5. The Klf family genes may be used either alone or in combinations of two or more. Among these Klf family genes, the present invention preferably uses Klf2 gene, Klf4 gene, and Klf5 gene, more preferably Klf2 gene and Klf4 gene, particularly preferably Klf4 gene. Klf4 gene is known as a tumor inhibitory factor (A. M. Ghaleb et al., Cell Res., 15, pp 92-96, 2005), and has known base sequences (NCBI accession Number NM_010637 (human), NM_004235 (Mouse)). Klf1 gene, Klf2 gene, and Klf5 gene also have known base sequences (NCBI accession Number NM_006563 (human), NM_010635 (Mouse)), (NCBI accession Number NM_016270 (human), NM_008452 (Mouse)), and (NCBI accession Number NM_001730 (human), NM_009769 (Mouse)), respectively.

SOX9 gene is known as a transcription factor that regulates the expression of, for example, type II collagen (V. Lefebvre et al., Mol. Cell. Biol. 17, pp 2336-2346, 1997), and has known base sequences (NCBI accession Number NM_000346 (human), NM_011448 (Mouse)). Replacing SOX9 gene with other SOX family gene leads to induction failure in the chondrocyte-like cells. Specifically, in the present invention, induction to the chondrocyte-like cells is only possible by the combination of Myc family gene and/or Klf family gene with SOX9 gene, and it is important that these genes hold a combined, nondivisible relationship with each other.

These three genes commonly exist in mammals including humans, and any of these genes originating mammals may be used. Desirably, these genes are appropriately selected according to the origin of the recipient somatic cells. For example, the three genes are desirably of human origin when the somatic cells used originate in humans. Further, the three genes may be wild-type genes, or mutated genes coding for mutated gene products that have the replacement, deletion, and/or insertion of several (for example, 1 to 10, preferably 1 to 6, more preferably 1 to 4, further preferably 1 to 3, particularly preferably 1 or 2) amino acids in the amino acid sequences, and that function in the same way as the wild-type gene products.

In the present invention, the three genes can be prepared according to an ordinary method, based on known sequence information. For example, the cDNA of the gene of interest can be prepared by extracting RNA from mammal-derived cells, followed by cloning using an ordinary method.

In the present invention, the genes introduced into the somatic cells may be a combination of SOX9 gene with at least one of the Myc family gene and the Klf4 family gene introduced as reprogramming factors. However, from the standpoint of improving the induction efficiency of the chondrocyte-like cells, the introduced genes are, for example, preferably a combination of SOX9 gene with at least one of Myc family genes and at least one of Klf family genes; more preferably a combination of SOX9 gene with c-Myc gene or N-Myc gene, and Klf2 gene or Klf4 gene; particularly preferably a combination of three genes, i.e., c-Myc gene, Klf4 gene, and SOX9 gene.

The two or more genes may be introduced into the somatic cells by using methods commonly used in animal cell transfections. Specific examples of the method that can be used to introduce the two or three genes into the somatic cells include methods using vectors; calcium phosphate method; lipofection method; electroporation method; and microinjection method. For introduction efficiency, methods using vectors are preferable. When the two or more genes are introduced into the somatic cells using vectors, the vectors may be, for example, virus vectors, non-virus vectors, or artificial viruses. Considering safety, virus vectors such as adenovirus and retrovirus are preferably used. Note that, when vectors are used, the two or more genes may be incorporated into different vectors, or may be incorporated in the same single vector.

Introducing the two or more genes into the somatic cells reprograms the somatic cells, and induces the somatic cells into proliferative chondrocyte-like cells that have the properties of the chondrocytes. The cells induced to chondrocyte-like cells can be selected from the somatic cells in which the two or more genes are introduced, based on the presence or absence of cell proliferative ability and the presence or absence of the properties comparable to the chondrocyte properties. Specifically, the chondrocyte-like cells can be selected from cells having a proliferative ability, using indices such as cell shape, the presence or absence of specific staining for the chondrocytes, and the presence or absence of chondrocyte marker gene expression in the cells. When the somatic cells include a reporter gene construct introduced therein after being constructed by binding a drug resistant gene to the promoter of a chondrocyte marker gene, cells that have acquired the cartilage properties can be selected by using cell growth in the presence of a drug as an index, because such cells can grow in the presence of a drug. Further, by taking advantage of the chondrocyte-like cells that assume a round or polygonal shape in a monolayer culture in liquid medium, these shapes also can be used as an index. Further, because the chondrocyte-like cells include glucosaminoglycan specifically expressed in chondrocytes, the presence or absence of glucosaminoglycan stained with alucian blue also can be used as an index. Further, because the chondrocyte-like cells express chondrocyte marker genes (such as Col2a1, Acan, and SOX5), the presence or absence of marker gene expression also can be used as an index.

The chondrocyte-like cells obtained as above can proliferate in a monolayer culture in liquid medium, stably grow generally up to about 9 to 21 passages while maintaining the chondrocyte properties. The chondrocyte-like cells can be cultured with media commonly used for culturing animal cells. DMEM medium containing about 1 to 25 volume % FBS is a preferred example of the medium used to culture the chondrocyte-like cells.

The thus-obtained chondrocyte-like cells, when applied to cartilage tissue in vivo, can form a new cartilage tissue of a three-dimensional structure using the cartilage tissue as a scaffold. When cultured in vitro in the presence of a scaffolding material, the chondrocyte-like cells can form a cartilage tissue of a three-dimensional structure.

As described thus far, the chondrocyte-like cells obtained in the present invention have a proliferative ability, and can regenerate cartilage tissue in an organism. The chondrocyte-like cells are thus effective for the treatment of cartilage disease such as osteochondrosis deformans, chondrodystrophy arthritis (for example, rheumatoid arthritis), trauma, and osteonecrosis, and can be used as a cell preparation (pharmaceutical composition) for cartilage tissue regeneration.

The chondrocyte-like cells may be applied to a cartilage disease site either alone or with a scaffolding material. When applied to a cartilage disease site with a scaffolding material, the chondrocyte-like cells may be applied to the cartilage disease site separately from the scaffolding material. However, it is desirable that the chondrocyte-like cells and the scaffolding material be applied to the cartilage disease site at the same time in the form of a cell preparation, as will be described later.

When the chondrocyte-like cells are prepared as a cell preparation for cartilage tissue regeneration, a pharmaceutically acceptable carrier for dilution may be contained with the chondrocyte-like cells, as required. Examples of pharmaceutically acceptable carriers for dilution include physiological salines, and buffers. Further, the cell preparation may also contain pharmacologically active components, and nutrient source components for the chondrocyte-like cells, as required.

Desirably, the cell preparation contains a scaffolding material for the chondrocyte-like cells. When the cell preparation contains a scaffolding material, it is desirable that the chondrocyte-like cells be contained by being supported on the scaffolding material. The use of scaffolding material improves the graft rate of the chondrocyte-like cells at the diseased site of cartilage tissue, and further promotes cartilage tissue regeneration.

The scaffolding material is not particularly limited, as long as it is pharmaceutically acceptable. The scaffolding material is appropriately selected according to the target site of cartilage tissue. For example, gelatinous or porous, biodegradable or bioresorbable materials can be used. Preferred examples of scaffolding material include collagen, hydroxyapatite, α-TOP (tricalcium phosphate), β-TOP (tricalcium phosphate), polylactic acid, polyglycolic acid, and complexes of these. The scaffolding materials may be used either alone or in combinations of two or more. Of these scaffolding materials, collagen is preferable from the standpoint of efficient cartilage tissue regeneration. When collagen is used as scaffolding material, the collagen is desirably prepared into a gel form of a three-dimensional structure.

The shape of the scaffolding material is not particularly limited, and is appropriately designed according to the shape of the damaged site of the cartilage tissue targeted by the cell preparation.

The chondrocyte-like cells can be supported on the scaffolding material by, for example, inoculating or mixing the chondrocyte-like cells with the scaffolding material, followed by culturing.

When the chondrocyte-like cells in the cell preparation are used by being supported on the scaffolding material or used to construct a cartilage tissue of a three-dimensional structure, the proportion of the chondrocyte-like cells with respect to the scaffolding material may be appropriately set according to such factors as the site of the targeted cartilage tissue and the type of scaffolding material. As an example, the chondrocyte-like cells are used in a proportion of $1\times10^6$ to $1\times10^8$ cells per 1 $cm^3$ of the scaffolding material.

The method used to apply the cell preparation to the diseased site of cartilage tissue is appropriately set according to such factors as the type of cell preparation and the site of the targeted cartilage tissue. For example, the cell preparation may be directly injected through an incision at the diseased site of the treated cartilage tissue or the cell preparation may be injected to the diseased site of the treated cartilage tissue using an arthroscope.

The dose of the cell preparation applied to the diseased site of cartilage tissue may be appropriately set to an amount effective for cartilage tissue regeneration, based on such factors as the type of cell preparation, the site of cartilage tissue, the extent of symptoms, and the age and sex of a patient.

Further, the chondrocyte-like cells may be used to construct a cartilage tissue of a three-dimensional structure in vitro, and this construct may be used as a cartilage tissue implant for the treatment of cartilage disease that involves cartilage defects such as in osteochondrosis deformans.

The chondrocyte-like cells can be used to construct a cartilage tissue of a three-dimensional structure by, for example, inoculating the chondrocyte-like cells in scaffolding material, and culturing the cells in a medium capable of growing a chondrocyte-like cell until a cartilage tissue of a three-dimensional structure is constructed. More specifically, about $1\times10^6$ to $1\times10^8$ chondrocyte-like cells may be inoculated per 1 $cm^3$ of scaffolding material, and cultured under 5% $CO_2$ conditions at 37° C. for about 1 to 4 weeks. The same scaffolding material used for the cell preparation can be used to construct a cartilage tissue of a three-dimensional structure. The shape of the scaffolding material may be appropriately set according to the shape of the implant of interest. The medium used to construct a cartilage tissue of a three-dimensional structure is not particularly limited, as long as it can grow the chondrocyte-like cells. For example, DMEM medium containing about 1 to 25 volume % FBS may be used. From the standpoint of clinical application, use of serum-free media of defined compositions (defined serum-free media) is desirable.

The thus-prepared cartilage tissue of a three-dimensional structure prepared as above is used as a cartilage tissue implant, either in the state containing the scaffolding material, or after removing the scaffolding material.

The method used to apply the implant to the diseased site of the cartilage tissue is appropriately set according to such factors as the shape of the implant and the site of the targeted cartilage tissue. For example, the implant may be directly incorporated through an incision at the diseased site of the treated cartilage tissue.

The chondrocyte-like cells also can form a cartilage tissue when administered to a site of an organism other than the cartilage tissue. Thus, the chondrocyte-like cells may be administered into the body of a mammal, and the cartilage tissue formed by the chondrocyte-like cells in the body of the mammal may be removed to obtain a cartilage tissue implant.

The mammals used for the production of such cartilage tissue implants may be humans, or non-human mammals such as mice, rats, hamsters, rabbits, cats, dogs, sheep, pigs, cows, goats, and monkeys. Further, in the production of the cartilage tissue implant, the administration site of the chondrocyte-like cells is not particularly limited. However, considering the ease of the removal of the newly formed cartilage tissue, the administration site is preferably under the skin, particularly under the skin of the back. Further, in the production of the cartilage tissue implant, the chondrocyte-like cells may be administered together with a scaffolding material, or alone without a scaffold. The chondrocyte-like cells can form a cartilage tissue of a sufficient size in an organism without the administration of a scaffold.

In the production of the cartilage tissue implant, the dose of the chondrocyte-like cells for mammals is not particularly limited, and may be generally about $10^4$ to $10^8$ cells, preferably about $10^5$ to $10^7$ cells. Formation of a cartilage tissue is recognized after 14 to 35 days, preferably after 21 to 28 days from the administration of the chondrocyte-like cells to mammals.

The cartilage tissue implant may be produced in the body of a cartilage disease patient, and the cartilage tissue so produced may be transplanted into the cartilage disease site of the patient. Specifically, the chondrocyte-like cells may be administered to a site of a cartilage disease patient other than the cartilage tissue, and a new cartilage tissue formed by the chondrocyte-like cells in the body of the patient may be removed and administered to the cartilage disease site of the patient for the graft treatment of cartilage disease.

Further, a non-human mammal including a cartilage tissue formed by the chondrocyte-like cells administered to the organism may be used as a tool for evaluating the efficacy of a tested substance for the cartilage tissue. Specifically, a non-human mammal that includes a cartilage tissue formed by the chondrocyte-like cells may be administered with a tested substance to determine and evaluate the efficacy of the tested substance for the cartilage tissue. As used herein, the "tested substance" refers to a substance to be evaluated for its efficacy for the cartilage tissue. Specific examples include a candidate substance of a therapeutic drug for cartilage disease.

Further, the chondrocyte-like cells can be used as a tool for elucidating the pathology of various cartilage diseases. The chondrocyte-like cells induced from human somatic cells are useful as a tool for the discovery and development of drugs for cartilage diseases.

2. Chondrocyte-Like Cell Preparation Composition

As described above, the chondrocyte-like cells can be prepared by introducing into somatic cells at least one gene selected from the group consisting of Myc family gene and Klf family gene, in combination with SOX9 gene. The present invention thus provides a chondrocyte-like cell preparation composition that includes SOX9 gene and at least one gene selected from the group consisting of Myc family gene and Klf family gene. The chondrocyte-like cell preparation composition includes a set of factors, namely, a reprogramming factor used to induce somatic cells to chondrocyte-like cells and a cartilage-inducible transcription factor. Desirably, the two or more genes are contained in a form introducible into the somatic cells. A specific example is a vector that has incorporated the two or more genes. The two or more genes may be incorporated in different vectors, or in the same single vector.

The types of the genes and vectors used for the chondrocyte-like cell preparation composition are as described above.

EXAMPLES

The present invention is described below based on Examples. Note, however, that the invention is not limited by the following descriptions.

Example 1

Production of Chondrocyte-Like Cells from Dermal Fibroblasts and Embryonic Fibroblasts 1. Production of Col11a2-β Geo Transgenic Mice Methods First, transgenic mice were produced that express β-geo (fused gene of β-galactosidase gene and neomycin resistant gene) under the control of Col11a2 promoter/enhancer sequences shown in FIG. 1, a, using the following procedure.

742LacZInt, an α2 (XI) collagen gene-based expression vector, includes a mouse Col11a2 promoter (−742 to +380), SV40 RNA splicing sites, a β-galactosidase reporter gene, an SV40 polyadenylation signal, and a 2.34-kb first intron sequence of Col11a2 as a enhancer (Reference Literature 1). In order to produce a β-geo introducing gene, a 0.8-kb neomycin resistant gene fragment was ligated to the 3'-end of a 3.1-kb cDNA fragment that codes for LacZ. The β-geo fragment was incorporated in a 742LacZInt expression vector at the Not I site by replacing the LacZ gene, and a Col11a2-β geo plasmid was produced.

The Col11a2-β geo plasmid was digested with EcoRI and PstI to release the inserts in the plasmid. The inserts were microinjected into the pronucleus of a F1 hybrid mouse (C57BL/6×DBA)-derived fertilized egg according to the method of Reference Literature 1 to produce a transgenic mouse. The transgenic mouse was identified by PCR assays of the genomic DNA extracted from the tail. Specifically, the transgenic mouse was identified by amplifying the genomic DNA by introduced gene-specific PCR, and by amplifying the 135-bp product specifically contained in the β geo transgenic mouse, using a primer (CGC TAC CAT TAC CAG TTG: SEQ ID NO: 1) that recognizes the LacZ gene, and a primer (CCA GTC ATA GCC GAA TAG: SEQ ID NO: 2) that recognizes the neomycin resistant gene. The transgenic mouse so identified was crossed with C57BL/6 mice for at least four generations.

The transgenic mouse prepared as above was studied by the X-gel staining of the whole body and slices, according to the method described in Reference Literature 2.

Results

The α2 (XI) collagen chain is a cartilage-specific matrix protein that supports the cartilage tissue structure, and has an important role in the impact absorbing functions of the cartilage. It is known that the expression of the Col11a2 promoter/enhancer sequences is cartilage specific (Reference Literature 1). The Col11a2 promoter has an insulator activity, and is believed to contribute to stable expression of the introduced gene in transgenic mouse. X-gal staining of the transgenic mouse showed LacZ activity specific to the chondrocytes, whereas no activity was observed in other tissues (see the left diagram in FIG. 1, b). Further, histological analysis confirmed β geo expression in all chondrocytes (see the right diagram in FIG. 1, b).

2. Separation and Analyses of Mouse Embryonic Fibroblasts, Adult Mouse Dermal Fibroblasts, and Primary Chondrocytes from Col11a2-β Geo Transgenic Mice Methods Mouse embryonic fibroblasts (MEFs), adult mouse dermal fibroblasts (MDFs), and primary chondrocytes were isolated according to the following procedure, using the transgenic mice obtained as above.

MEFs were separated according to the method of Reference Literature 3. Specifically, first, the head and the gut tissue were removed from a 13.5 dpc embryo. The remaining body part was finely sliced, and transferred to a tube after trypsin treatment. Cells were collected by centrifugation, and suspended in DMEM medium that contained 10% FBS. The cells ($1 \times 10^6$) were cultured in a 100-mm dish to obtain MEFs (first passage).

MDFs were prepared from the transgenic mouse, 3 to 6 months of age. Specifically, after shaving the transgenic mouse, the skin was sectioned, and subjected to trypsin treatment at 37° C. for 4 hours. The free cells were filtered through a nylon mesh (pore size, 40 µm; Tokyo Screen, Tokyo, Japan) to produce a single-cell suspension, which was then cultured in a 100-mm dish to obtain MDFs (first passage).

The primary chondrocytes were separated according to the method of Reference Literature 4. Specifically, the transgenic mouse was dissected, and the epiphyseal cartilages of the humerus and femur were collected by separating the tissue in a DMEM medium that contained 2% FBS and streptomycin/penicillin. The cohesive tissue and the cartilage membrane of the epiphyseal cartilage were physically removed after digestion with collagenase (type II, Sigma) at 37° C. for 30 min (2 mg/ml in DMEM/2% FBS). After the removal of the cohesive tissue and the cartilage membrane, the epiphyseal cartilage was treated in a collagenase solution for 2 to 4 hours to free the primary chondrocytes. The free cells were collected by centrifugation (200×g at 4° C. for 5 min), and suspended in a fresh medium. The cells were inoculated in a 60-mm or 100-mm dish, and cultured in a 2% FBS-containing DMEM medium to obtain the primary chondrocytes.

Note that the first passages of MEFs and MDFs were cryopreserved in liquid nitrogen after the trypsin treatment, and later used for testing (described later).

The primary chondrocytes were evaluated for LacZ activity by X-gal staining.

The primary chondrocytes, MEFs, and MDFs were added to media that contained 0 to 900 µg/ml G418 (Geneticin), and incubated under 5% $CO_2$ conditions at 37° C. to evaluate cell growth. Note that 2% FBS-containing DMEM medium was used for the primary chondrocyte culture, and 10% FBS-containing DMEM medium for the MEF and MDF cultures. For comparison, primary chondrocytes prepared from a wild-type littermate mouse using the same technique were also incubated in the presence of G418 to evaluate cell growth.

Results

About 50% of the cells in the primary chondrocytes prepared from the β geo transgenic mouse were stained by X-gal staining (see FIG. 1, c). This result suggests that the chondrocytes had dedifferentiated, or contamination of the fibroblasts in the fibrous tissue attached to the cartilage had occurred during the preparation.

FIG. 1 in d shows the results of the incubation of the primary chondrocytes, MEFs, and MDFs in the presence of G418 after preparation from the β geo transgenic mouse. In contrast to the MEFs and MDFs that died out completely in the presence of 300 µg/ml G418, the primary chondrocytes prepared from the transgenic mouse grew even in the presence of 900 µg/ml G418. The majority of the primary chondrocytes prepared from the wild-type F1 hybrid mouse (C57BL/6×DBA) died in the presence of 300 µg/ml G418.

3. Assessment of Factors that Induce MEFs to Chondrocytes

Methods

The factors that induce somatic cells to chondrocytes were identified by evaluating the presence or absence of induction to chondrocytes through transformation of the MEFs using four reprogramming factors (Oct3/4, Sox2, c-Myc, and Klf-4), and a cartilage-inducible transcription factor (Sox9). Because cells showing a chondrocyte phenotype have resistance to G418, the test confirmed the presence or absence of induction to chondrocytes using G418 resistance as an index. Specifically, the test was performed according to the following procedure.

In this test, the reprogramming factors and the cartilage-inducible transcription factor were introduced into somatic cells using the retro virus pMXs/Plat-E vector system as in the method of Reference Literature 3. Specifically, the following retro virus vectors were used: A retro virus vector having incorporated mouse c-Myc (pMXs-c-Myc), a retro virus vector having incorporated mouse Klf4 (pMXs-Klf4), a retro virus vector having incorporated mouse Sox2 (pMXs-Sox2), and a retro virus vector having incorporated mouse Oct3/4 (pMXs-Oct3/4). Human SOX9 was incorporated in a retro virus vector by incorporating human SOX9 cDNA in a Gateway pENTR-1A vector (Invitrogen), and by inserting the resulting plasmid into pMXs-gw using LR reaction (Invitrogen).

The transcription factor was introduced to somatic cells according to the following procedure. First, $8\times10^6$ Plat-E cells were inoculated in a 10-ml 10% FBS-containing DMEM medium (1 µg/ml puromycin, 10 µg/ml brastcidine, supplemented with penicillin and streptomycin) in a 100-mm dish, and the Plat-E cells were transfected with each pMXs-based retro virus vector on the next day, using Fugene 6 transfection reagent (Roche). The medium was exchanged 24 hours after the transfection. Twenty-four hours after the medium exchange, the medium was collected as a virus-containing supernatant from the Plat-E culture.

The cryopreserved MEFs were inoculated in a 100-mm dish. The MEFs or MDFs were subjected to trypsin treatment a day before transfection, and $5\times10^5$ cells in a 100-mm dish were statically cultured in 10% FBS-containing DMEM medium for 24 hours (third passage).

Each virus-containing supernatant obtained as above was then filtered through a 0.45-µm cellulose acetate filter (Schleicher & Schuell), and polybrene (Nacalai Tesque) was added to the resulting filtrate at a final concentration of 4 mg/ml to prepare a virus solution. Each virus solution was mixed according to the combination of transfecting genes to prepare a mixed virus solution. Note that each virus solution to be mixed in the preparation of the mixed virus solution was set so as to contain the retro virus vectors in equal amounts.

The virus solution or virus mixture was then added to the cultured MEF dish, and incubated at 37° C. for 16 hours for transfection with the retro virus vector. After being incubated, the cells in the dish were treated with trypsin, and statically cultured for 2 days in three 10-cm dishes that contained fresh DMEM medium supplemented with 10% FBS. The medium was exchanged with 10% FBS-containing DMEM medium supplemented with 500 µg/ml G418, and the cells were statically cultured for two weeks while exchanging the medium with a medium of the same composition every other day.

The thus-cultured cells were stained with alucian blue, and then with crystal violet, and the stained colonies in each dish were counted. The number of stained colonies was measured by counting the total number of stained colonies in the three dishes. Note that only the cells differentiated into the chondrocytes are stained, because alucian blue stains the glucosaminoglycan specifically expressed in the chondrocytes, while crystal violet stains all the cells.

For comparison, MEFs were transformed using a retro virus vector (pMXs-EGFP) having incorporated GFP cDNA, and the transformed cells were evaluated, using the same techniques described above.

Results

Figure 2:
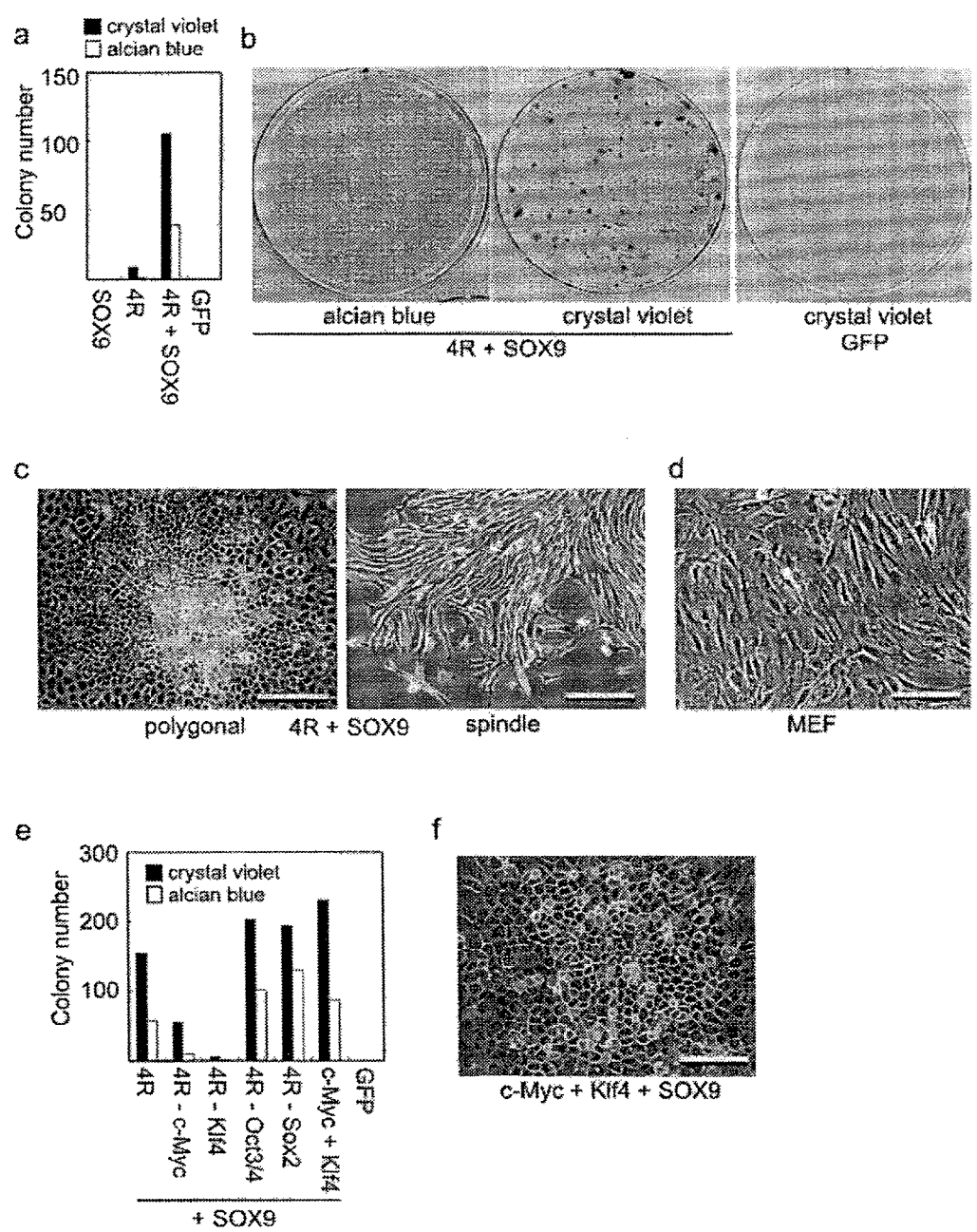
FIG. 2 is a diagram representing the analysis results for the cells produced by introducing each factor into MEFs; a, the number of stained colonies counted after the alucian blue staining and crystal violet staining of the colonies obtained by introducing each factor into MEFs, in which "4R" represents four reprogramming factors (Oct3/4, Sox2, c-Myc, and Klf-4), also used in the other figures in the same meaning; b, the results of the alucian blue staining and crystal violet staining of the cells obtained by transfecting MEFs with the four reprogramming factors (Oct3/4, Sox2, c-Myc, and Klf-4) in combination with human SOX9; c, the results of observing the shape of the cells contained in the colonies obtained by transfecting MEFs with the four reprogramming factors (Oct3/4, Sox2, c-Myc, and Klf-4) in combination with human SOX9; d, the result of observing MEF shape; e, the number of colonies counted after the alucian blue staining and crystal violet staining of the colonies obtained by introducing three reprogramming factors and Sox9, in which "4R-c-Myc" means the four reprogramming factors (Oct3/4, Sox2, c-Myc, and Klf-4) minus c-Myc, "4R-Klf4" means the four reprogramming factors (Oct3/4, Sox2, c-Myc, and Klf-4) minus Klf-4, "4R-Oct3/4" means the four reprogramming factors (Oct3/4, Sox2, c-Myc, and Klf-4) minus Oct3/4, and "4R-Sox2" means the four reprogramming factors (Oct3/4, Sox2, c-Myc, and Klf-4) minus Sox2; the same denotation is also used in the other figures in the same meaning; f, the results of observing the shape of the cells contained in the colonies obtained by transfecting MEFs with c-Myc, Klf4, and Sox9.

FIG. 2 shows the analysis results for the cells produced by introducing each factor to MEFs. FIG. 2 in a represents colony numbers counted after the alucian blue staining and crystal violet staining of the cells produced by introducing each factor to MEFs. FIG. 2b represents the results of alucian blue staining and crystal violet staining for the cells obtained by transfecting the MEFs with the four reprogramming factors (Oct3/4, Sox2, c-Myc, and Klf-4) in combination with human SOX9. MEF transfection with human SOX9 alone did not induce colony formation in the presence of G418 (FIG. 2, *a*). In the transfection of MEFs only with the four reprogramming factors (Oct3/4, Sox2, c-Myc, and Klf-4), formation of small numbers of colonies of spindle-shaped cells of non-chondrocyte-like morphology was observed. However, these colonies were not stained with alucian blue, and were not differentiated chondrocytes. On the other hand, about 110 G418-resistant colonies per 10-cm dish were observed in the transfection of MEFs with the four reprogramming factors in combination with SOX9, and about 30% of these colonies were stained with alucian blue (see FIGS. 2, *a* and *b*). The cells obtained by transfecting the MEFs with the four reprogramming factors in combination with SOX9 had shapes that varied from colony to colony, some being colonies of polygonal cells (left in FIG. 2, *c*)—similar in shape to the primary chondrocytes (FIG. 1, *c*)—, and other being colonies of spindle shaped cells (right in FIG. 2, *c*), as with the MEFs (FIG. 2, *d*).

In order to identify the importance of each factor on the formation of G418-resistant colonies, MEFs were transfected with three of the four reprogramming factors and Sox9, and the resulting cells were analyzed. FIG. 2 in *e* represents colony numbers counted after the alucian blue staining and crystal violet staining of the cells to which three reprogramming factors and Sox9 were introduced. The average colony number was found to decrease in the absence of c-Myc or Klf4. On the other hand, the colonies did not decrease even without the introduction of Oct3/4 or Sox2. These results suggest that the transfection by c-Myc, Klf4, and Sox9 is important for the induction of MEFs to chondrocytes. In the transduction of MEFs with c-Myc, Klf4, and Sox9, about 50% of about 250 G418-resistant colonies were formed by polygonal cells of chondrocyte-like morphology (see FIG. 2, *f*).

4. Assessment of Factors that Induce MDFs to Chondrocytes
Methods

Figure 3:
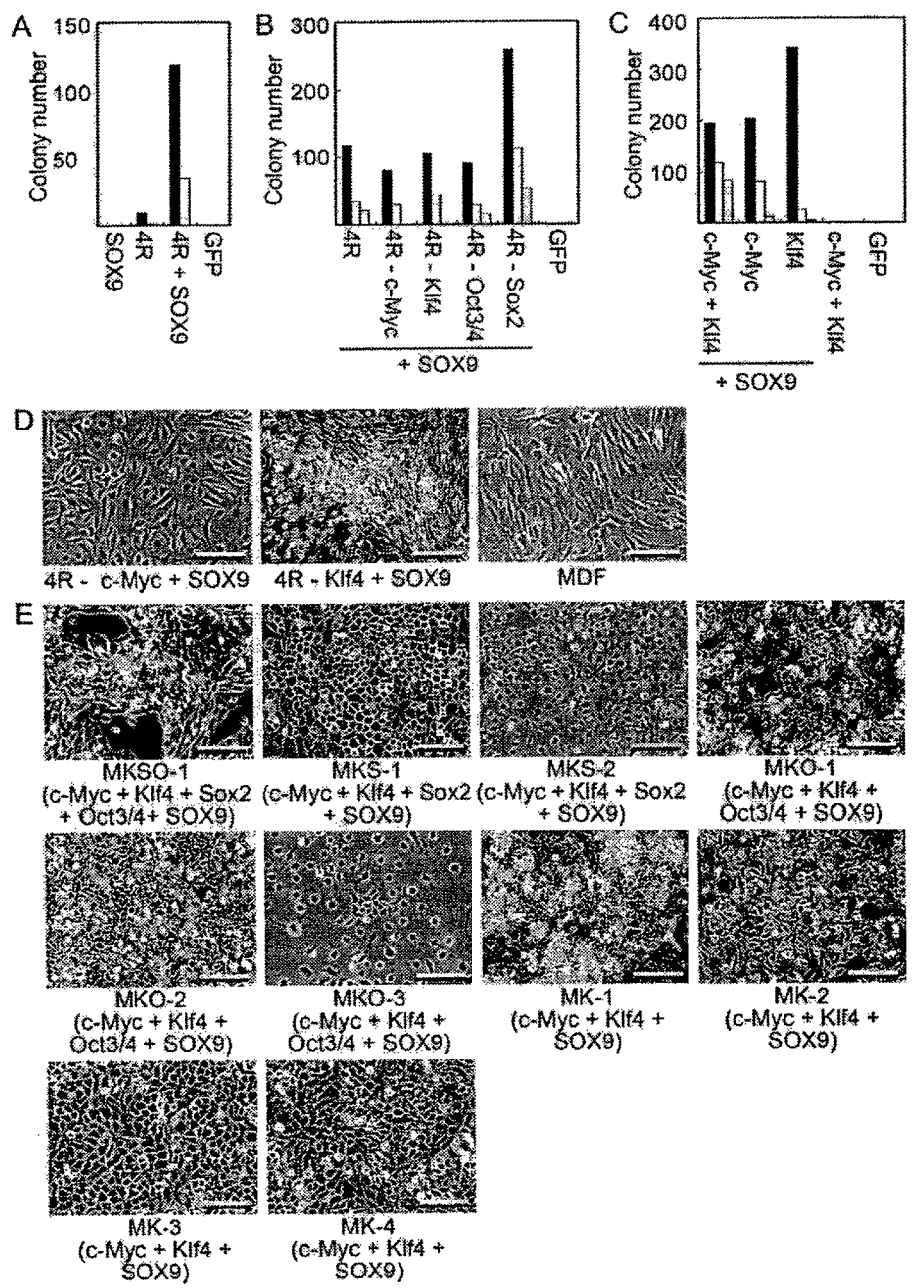
FIG. 3 is a diagram representing the analysis results for the cells produced by introducing each factor into MDFs; A to C, the number of stained colonies counted after the alucian blue staining and crystal violet staining of the colonies obtained by introducing different factors to MDFs in various combinations, and the number of colonies formed by polygonal cells; D, the results of observing the morphology of the cells contained in the colonies obtained by introducing each factor to MDFs; E, the results of observing the shape of each cell after culturing the cells contained in the colonies obtained by introducing each factor to MDFs.

MDFs were transfected with various combinations of the four reprogramming factors (Oct3/4, Sox2, c-Myc, and Klf-4) and the cartilage-inducible transcription factor (SOX9) using the foregoing technique, and the properties of the resulting cells were analyzed.
Results FIG. 3 represents the analysis results for the cells obtained by introducing each factor to MDFs. FIG. 3A to C represents colony numbers counted after the alucian blue staining and crystal violet staining of the cells produced by introducing each factor to MDFs, and the number of colonies of polygonal cells. MDF transfection with SOX9 alone did not induce colony formation in the presence of G418 (see FIG. 3, A). Only small numbers of colonies were formed in the transfection of MDFs only with the four reprogramming factors (Oct3/4, Sox2, c-Myc, and Klf-4). On the other hand, about 120 G418-resistant colonies resulted from the MDFs transduced with the four reprogramming factors (Oct3/4, Sox2, c-Myc, and Klf-4) in combination with SOX9, and about 30% of these colonies were formed by polygonal cells of chondrocyte-like morphology. These results obtained from MDFs had the same tendency as the results obtained from MEFs (see FIG. 2, *a*).

The colony number slightly decreased when any of the c-Myc, Klf4, and Oct3/4 were lacking from the four reprogramming factors (Oct3/4, Sox2, c-Myc, and Klf-4) in the presence of SOX9, whereas the colony number increased when Sox2 was lacking (see FIG. 3, B). Colonies formed by round or polygonal cells were not observed in the colonies when either c-Myc or Klf4 was lacking from the four reprogramming factors in the presence of SOX9 (FIG. 3, B), and about ⅓ of the colonies were formed by round or polygonal cells when Oct3/4 was lacking from the four reprogramming factors in the presence of SOX9 (see FIG. 3, B). These results suggest that c-Myc, Klf4, and SOX9 are important in the formation of colonies that include G418-resistant cells of a chondrocyte-like shape from MDFs. Specifically, it was found that the combination of c-Myc, Klf4, and SOX9 produced about 200 G418-resistant colonies from MDFs, and that about 40% of these colonies were formed by round or polygonal cells (see FIG. 3, C). The combination of c-Myc and SOX9 also formed about 200 G418-resistant colonies. Although most of these colonies were formed by spindle-shaped or more flat cells of non-chondrocyte-like morphology, colonies formed by round or polygonal cells of chondrocyte-like morphology were also observed, though in small numbers (see FIG. 3, C). Further, about 350 G418-resistant colonies were formed with the combination of only SOX9 and Klf4, and these colonies included colonies formed by small numbers of round or polygonal cells of chondrocyte-like morphology (see FIG. 3, C).

As demonstrated by the foregoing results, the introduction of c-Myc, Klf-4, and SOX9 created about 50 colonies of G418-resistant cells of chondrocyte-like morphology from $5 \times 10^5$ MDF cells. Adding Oct3/4 to the combination of these three factors did not influence the number of colonies formed by the G418-resistant cells of chondrocyte-like morphology. Colony formation was impeded by addition of Sox2. Further, formation of G418-resistant colonies by the cells of chondrocyte-like morphology was also observed with both the combination of c-Myc and SOX9, and the combination of Klf-4 and SOX9. The results also suggested that the Sox2 introduction inhibits the induction to the cells of chondrocyte-like morphology.

On the other hand, formation of G418-resistant colonies was not observed when SOX5 and SOX6, used in place of SOX9, were introduced to MDFs with c-Myc and Klf-4 using the same technique. SOX5 and SOX6 are known to have supportive action for SOX9, but do not have the transactivation domain present in SOX9. Considering this, the transactivation domain present in SOX9 is likely to be involved in the induction to the cells of chondrocyte-like morphology.

Genes belonging to the Myc family and the Klf family basically have the same biological activity distinct to the family. The foregoing experimental results thus show that the use of the genes of the Myc family and the genes of the Klf family in combination with SOX9 enables induction of somatic cells to the cells of chondrocyte-like morphology.

5. Clone Production
Methods

The following eleven colonies were selected from the G418-resistant colonies induced from the MDFs, and clones were produced.

One from the colonies produced by the transfection with c-Myc, Klf-4, Sox2, Oct3/4 and Sox9 (clones will be denoted as MKSO-1)

Two from the colonies produced by the transfection with c-Myc, Klf4, Sox2, and Sox9 (clones will be denoted as MKS-1 or MKS-2)

Four from the colonies produced by the transfection with c-Myc, Klf4, Oct3/4, and Sox9 (clones will be denoted as MKO-1 to MKO-4)

Four from the colonies produced by the transfection with c-Myc, Klf4, and Sox9 (clones will be denoted as MK-1 to MK-4)

Each target colony was subjected to trypsin treatment, and cells were collected. The cells are cultured in a 10% FBS-containing DMEM medium supplemented with 500 µg/ml G418 under 5% CO₂ conditions at 37° C. for 6 to 10 days in a 96-well plate. The cells proliferated in the 96-well plates were transferred to a 24-well plate, and cultured under 5% CO₂ conditions at 37° C. for 24 to 31 days. The proliferated cells in the 24-well plate were transferred to a 6-well plate, and cultured under 5% CO₂ conditions at 37° C. for 18 to 31 days. The cells were transferred to a 10-cm dish, and the cells at this stage were defined as a fourth passage. The proliferated cells were cultured in a DMEM medium supplemented with 500 µg/ml. G418 and 10% FBS, and subcultured every six days.

Results

Upon culturing the cells contained in the eleven colonies using G-418-containing medium according to the foregoing method, the MKO-4 colony-derived cells stopped proliferating after the seventh passage. After culturing, ten clones (MKSO-1, MKS-1, MKS-2, MKO-1 to MKO-3, and MK-1 to MK-4) but MKO-4 were produced. Each clone was polygonal in shape, and had the morphology of chondrocytes (see FIG. 3, E).

6. Evaluation of Cloned Cell Properties

The cloned cells were analyzed by alucian blue staining, introduced-gene expression analysis, chondrocyte marker gene expression analysis, karyotyping, gene expression pattern analysis, the analysis of methylated CpG dinucleotide in the Col1a2 promoter region, and the analysis of proliferative properties.

6-1. Analysis by Alucian Blue Staining

The cloned cells (sixth passage), and MDFs (third passage) were cultured in a 10% FBS-containing DMEM medium supplemented with 500 µg/ml G418 in a 60-mm dish, and further cultured for 14 days after confluence. The cultured cells were then subjected to alucian blue staining.

Figure 4:
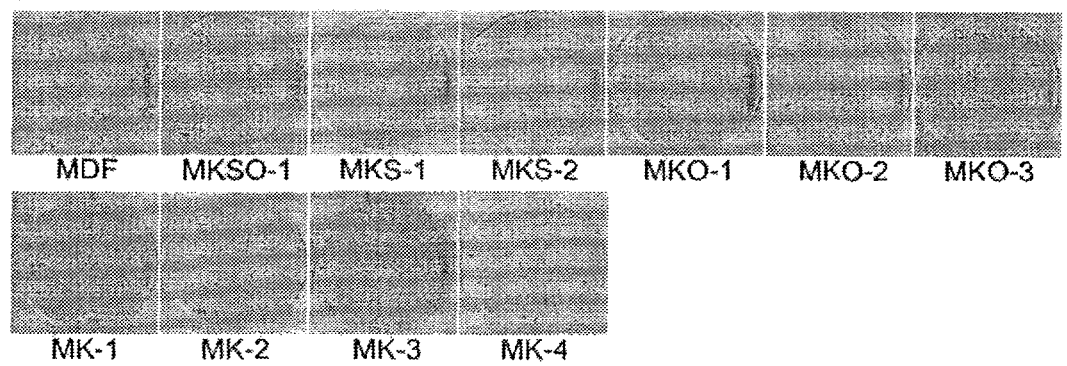
FIG. 4 is a diagram representing the results of evaluating the properties of the cells (cloned cells) obtained by introducing each factor to MDFs; A, the results of the alucian blue staining of MDFs and the cells obtained by introducing each factor to MDFs; B, the analysis results for the expression of the introduced genes (introduced factors) in MDFs, primary chondrocytes, and the cells obtained by introducing each factor to MDFs, in which "Pr chond." means primary chondrocytes, also used in the other figures in the same meaning; C, the results of analyses for the expression of the introduced genes (introduced factors) in MDFs, primary chondrocytes, and the cells obtained by introducing each factor to MDFs.
Figure 4:
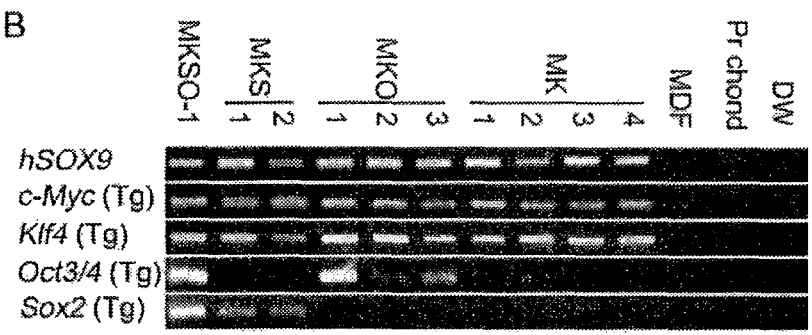
Figure 4:
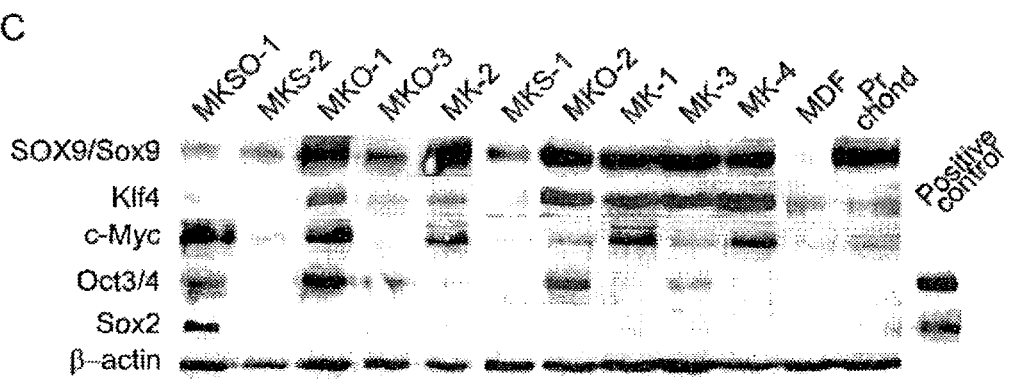

FIG. 4A shows the results. The cultured cells were strongly stained with alucian blue, verifying the presence of glycosaminoglycan. Note that the strength of staining varied among the clones.

6-2. Introduced-Gene Expression Analysis

Expression of the introduced genes in the cloned cells was analyzed by RT-PCR and western blotting, using primers that amplify the transcripts derived from the genes introduced to retro virus, but do not amplify the transcripts of the endogenous genes. Specifically, the analysis was performed according to the following procedure.

The cloned cells (sixth passage) and MDFs (third passage) were cultured in a 10% FBS-containing DMEM supplemented with 500 µg/ml G418, and the primary chondrocytes (first passage) prepared from β geo transgenic mouse were cultured in a 2% FBS-containing DMEM medium, each in a 60-mm dish. After confluence, total RNA in the cells was extracted using RNeasy Mini Kits (Qiagen, Santa Clarita, Calif.). The extracted total RNA was digested with DNase, and contaminating genomic DNA was removed. The resulting total RNA (1 µg) was then reverse-transcribed into a single-stranded (first-strand) cDNA using QuantiTect Reverse Transcription (Qiagen). The resulting cDNA (2 µl) was PCR amplified in a mixture (20 µl) containing ExTaq (Takara Bio) and primers (4 pmol) specific to each gene, and the RNA expression level of each gene was measured. Table 1 below lists the primers used.

TABLE 1

| Target gene | Primers used | Sequence |
|---|---|---|
| Klf4 | Klf4 Tg RT S | GACCACCTTGCCTTACACA |
|  | Klf4 Tg RT AS | CCCTTTTTCTGGAGACTAAAT |

TABLE 1-continued

| Target gene | Primers used | Sequence |
|---|---|---|
| c-Myc | c-Myc Tg RT S | TCGCTACCATTACCAGTTG |
|  | c-Myc Tg RT AS | CCCTTTTTCTGGAGACTAAAT |
| Oct3/4 | Oct3/4 Tg RT S | TCCCATGCATTCAAACTG |
|  | Oct3/4 Tg RT AS | CCCCTGTTGTGCTTTTAATC |
| Sox2 | Sox2 Tg RT S | CCATTAACGGCACACTGC |
|  | Sox2 Tg RT AS | CCTTACGCGAAATACGGG |
| hSOX9 | SOX9 RT S | CCAGCGAACGCACATCAA |
|  | SOX9 RT AS | GGAGTTCTGGTGGTCGGTGTA |

The cloned cells (sixth passage) and MDFs (third passage) were cultured in a 10% FBS-containing DMEM supplemented with 500 µg/ml G418, and the primary chondrocytes (first passage) prepared from β geo transgenic mouse were cultured in a 2% FBS-containing DMEM medium, each in a 60-mm dish. The cells were lysed after confluence. The cell lysate was subjected to sodium dodecyl sulfate-polyacrylamide gel electrophoresis (SDS-PAGE), followed by electroblotting and immunostaining. The antibodies used are anti-Sox9 antibodies (Santa-Cruz Biotechnology, Inc., 1:200 dilution), anti-c-Myc antibodies (Santa-Cruz Biotechnology, Inc., 1:200 dilution), anti-Klf4 antibodies (Santa-Cruz Biotechnology, Inc., 1:200 dilution), anti-Oct3/4 antibodies (Santa-Cruz Biotechnology, Inc., 1:600 dilution), anti-Sox2 antibodies (Santa-Cruz Biotechnology, Inc., 1:200 dilution), and anti-β-actin antibodies (Cell Signaling Technology, 1:5,000 dilution).

FIG. 4B shows the results of RT-PCR analysis, and FIG. 4C shows the results of western blotting. Expression of the introduced genes in the clones was confirmed from the results of RT-PCR analysis. Western blotting confirmed expression of the introduced genes in the clones cells at the protein level, but did not confirm expression of these genes in MDFs.

6-3. Chondrocyte Marker Gene Expression Analysis

Expression of chondrocyte marker genes in the cloned cells was analyzed by RT-PCR. Specifically, total RNAs were obtained from the cloned cells (sixth passage), MDFs (third passage), and the primary chondrocytes (first passage) prepared from β geo transgenic mouse using the foregoing technique, and the expression of chondrocyte marker genes (Col2a1, Acan, Hapln1, Sox5, Sox6, Col1a1, Col9a2, Col9a3, Col11a1, Col11a2) and MDF marker genes (Col1a1, Col1a2, Gapdh, RT-) was analyzed by RT-PCR analysis. The primers used are listed in Table 2.

TABLE 2

| Target gene | Primers used | Sequence |
|---|---|---|
| Gapdh | Gapdh RT S | GAGATGATGACCCTTTTGGCT |
|  | Gapdh RT AS | TCAAGGCCGAGAATGGGAAG |
| Sox5 | Sox5 RT S | CCCCTCAAAGCCTCTGTC |
|  | Sox5 RT AS | CTTGCTGCTCTCGCCTGA |
| Sox6 | Sox6 RT S | TCATCCCGGCCTAAGACA |
|  | Sox6 RT AS | ACAGGGCAGGAGAGTTGAG |
| Col2a1 | Col2a1 RT S | TTGAGACAGCACGACGTGGAG |
|  | Col2a1 RT AS | AGCCAGGTTGCCATCGCCATA |
| Col11a1 | Col11a1 RT S | ATGAGTATGCACCTGAGGAT |
|  | Col11a1 RT AS | GGAGTCTCAGTCTGGTAAGGTT |

TABLE 2-continued

| Target gene | Primers used | Sequence |
|---|---|---|
| Col11a2 | Col11a2 RT S | GACTGTAAGAAGCGAGTTACC |
| | Col11a2 RT AS | GCCTTCAAAGACTTCATCG |
| Col9a1 | Col9a1 RT S | TGTAGACTTCAGGATTCCAAC |
| | Col9a1 RT AS | CCAAATGTTCCAGTGCTT |
| Col9a2 | Col9a2 RT S | TGGAAGGGAGTGCGGATT |
| | Col9a2 RT AS | CGACCAGGATCACCCAGAAT |
| Col9a3 | Col9a3 RT S | TGGTGTGCCGGGACTTGAT |
| | Col9a3 RT AS | CACCCAGCTCGCCAGTTCTA |
| Col1a1 | Col1a1 RT S | GCAACAGTCGCTTCACCTAC |
| | Col1a1 RT AS | GTGGGAGGGAACCAGATTG |
| Col1a2 | Col1a2 RT S | TCGGGCCTGCTGGTGTTCGTG |
| | Col1a2 RT AS | TGGGCGCGGCTGTATGAGTTCTTC |
| Acan | Acan RT S | CCCTCGGGCAGAAGAAAGAT |
| | Acan RT AS | CGCTTCTGTAGCCTGTGCTTG |

Figure 5:
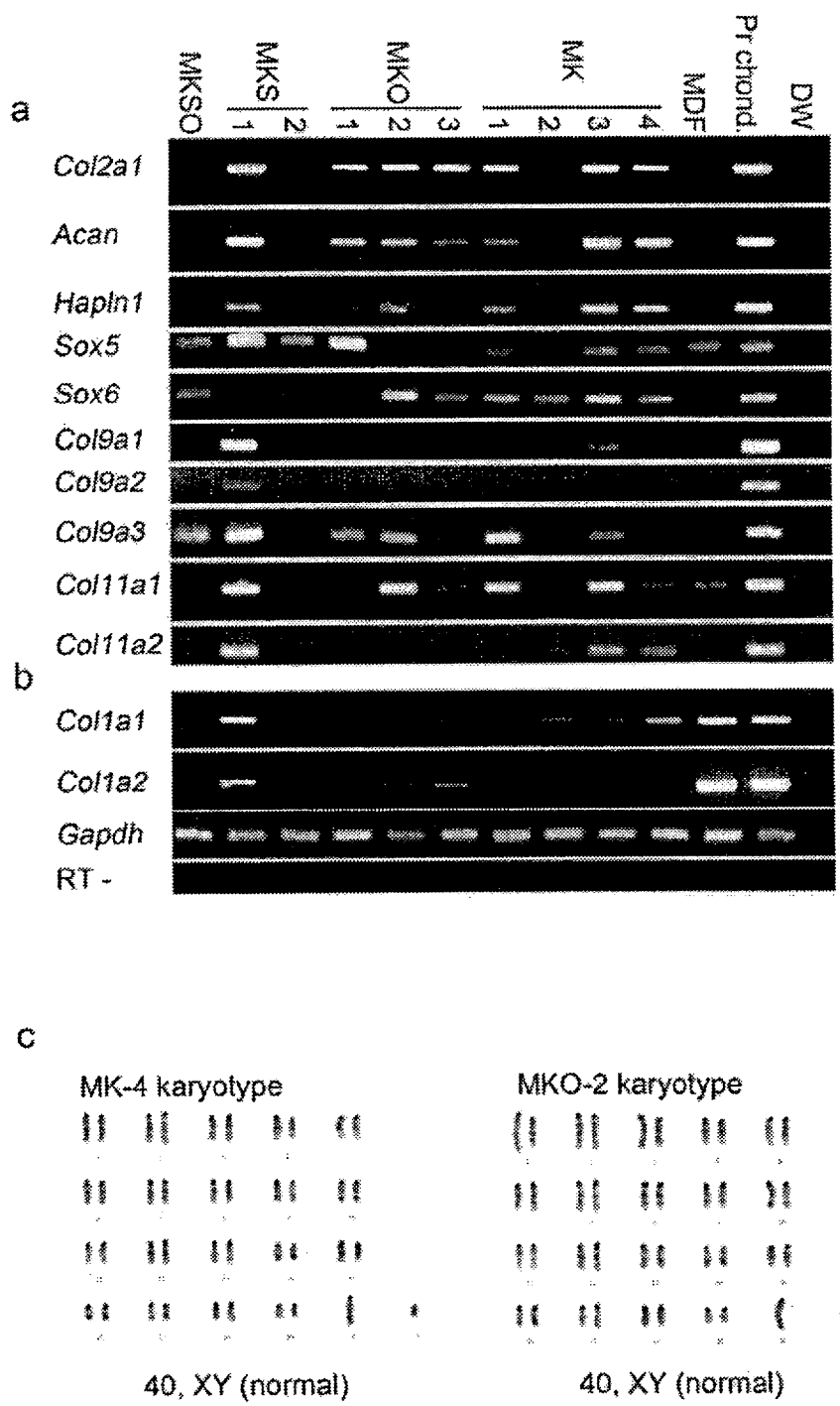
FIG. 5 is a diagram representing the results of evaluating the properties of the cells (cloned cells) obtained by introducing each factor to MDFs; a, the analysis results for the expression of chondrocyte marker genes in MDFs, primary chondrocytes, and the cells obtained by introducing each factor to MDFs; b, the analysis results for the expression of chondrocyte marker genes in MDFs, primary chondrocytes, and the cells obtained by introducing each factor to MDFs; c, the results of the karyotyping of the cells (MK-4, MKO-2) obtained by introducing each factor to MDFs.

FIG. 5a represents the results of the chondrocyte marker gene expression analysis, and FIG. 5b represents the results of the MDF marker gene expression analysis. The results showed that the cloned cells were capable of expressing the chondrocyte marker genes at various levels. MKS-1, MKO-2, MK-1, MK-3, and MK-4 expressed the chondrocyte marker genes, whereas MKS-2 and MK-2 did not express these genes. It was also confirmed that MKS-1 expressed fibroblast-specific type I collagen genes (Col1a1 and Col1a2).

Further, the presence of LacZ-negative cells in the primary chondrocytes prepared from β geo transgenic mouse raises the possibility that the perifibrous tissue-derived fibroblasts adhered to the cartilage were contaminated (see FIG. 1, c). This might explain the detection of the type I collagen gene (Col1a1 and Col1a2) mRNA, thought to be expressed in fibroblasts but not in pure chondrocytes, from the primary chondrocyte-derived RNA.

6-4. Karyotyping

The cloned cells were karyotyped by quinacrine-Hoechst staining. The analysis was performed at the International Council for Laboratory Animal Science (ICLAS) Monitoring Center (Japan).

FIG. 5c represents a part of the results. MKS-2, MKO-2, and MK-4 had normal 40XY karyotypes, whereas MK-3 was a mixture of normal 40XY and 41XY+4.

6-5. Gene Expression Pattern Analysis

The overall gene expression pattern of the cloned cells (MKS-1, MKO-2, MKl-1, MK-3, MK-4), MDFs, and the primary chondrocytes prepared from β geo transgenic mouse was analyzed as follows, using scatter plots in DNA microarray analysis.

A biotin-labeled cRNA was obtained from 250 ng of total RNA, using a Message Amp III RNA Amplification Kit (Ambion). Ten micrograms of the fragmented cRNA were then hybridized against an Affymetrix 430 2.0 Gene Chip array at 45° C. for 16 hours. The DNA chip was washed, and stained further. The resulting DNA chip was scanned using Affymetrix Fluidics station 450 and a scanner, and the resulting image was analyzed using GCOS software. For normalization, calculations were performed using MAS 5.0 algorithm. Cluster analyses were performed using Cluster 3.0 (The University of Tokyo).

Figure 6:
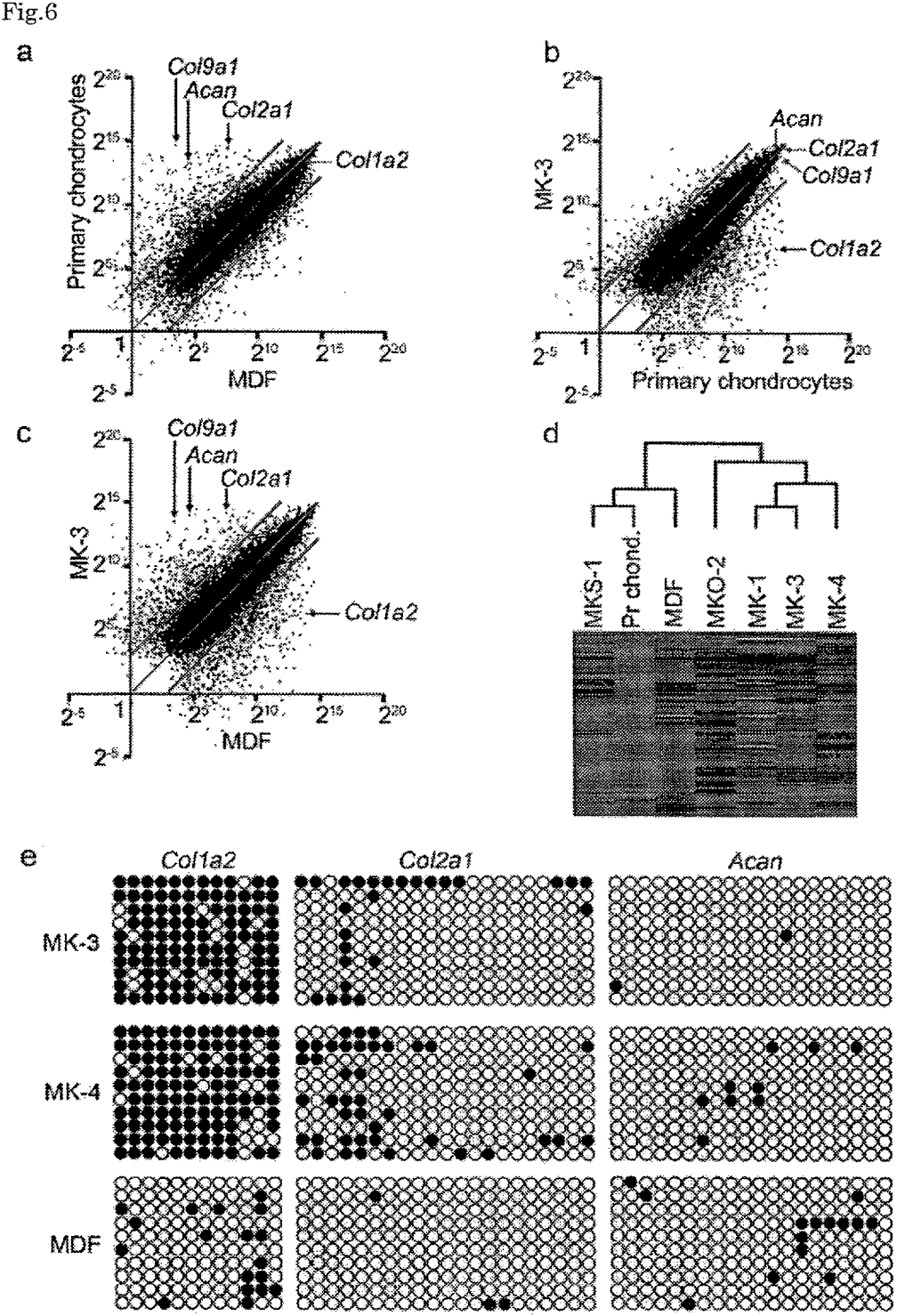
FIG. 6 is a diagram representing the results of evaluating the properties of the cells (cloned cells) obtained by introducing each factor to MDFs; a, a diagram comparing gene expression patterns for primary chondrocytes and MDFs; b, a diagram comparing gene expression patterns for MK-3 and primary chondrocytes; c, a diagram comparing gene expression patterns for MK-3 and MDFs; d, the result of the cluster analyses of MDFs, primary chondrocytes, and the cells obtained by introducing each factor to MDFs; e, the results of the bisulfite genomic sequencing analyses of MK-3, MK-4, and MDFs concerning the dinucleotide methylation status, in which the solid dots represent methylated CpG dinucleotide in each gene, and open dots represent unmethylated CpG dinucleotide in each gene.

The results of scatter plots in the DNA microarray analysis are presented in FIG. 6, a to c. The number of overexpressed genes was smaller in the MDFs as measured against the primary chondrocytes, whereas the number of overexpressed genes was greater in the primary chondrocytes as measured against the MDFs (see FIG. 6, a). This result coincides with the implication that the primary chondrocytes were contaminated with the fibroblasts. Further, the number of overexpressed genes in MK-3 measured against the primary chondrocytes (see FIG. 6, b) was smaller than that in MK-3 measured against the MDFs (see FIG. 6, c). Further, the number of overexpressed genes in the primary chondrocytes measured against MK-3 (see FIG. 6, b) was about the same as that in MDFs measured against MK-3 (see FIG. 6, c). This is considered to be due to the contamination of the primary chondrocytes with the fibroblasts. These results suggest that MK-3 is similar to pure chondrocytes at the overall transcription level. In both MK-3 and primary chondrocytes, the expression levels of the cartilage matrix genes including Col2a1, aggrecan gene (Acan), and Col9a1 were considerably higher than the expression levels of the other genes (see FIG. 6, b).

The results of the cluster analyses are presented in FIG. 6, d. It became clear from the results of cluster analyses that the cloned cells other than MKS-1 were classified in different clusters from those of the MDFs, primary chondrocytes, and MKS-1. This coincides with the RT-PCR finding that MKS-1 expresses both chondrocyte marker genes and MDF marker genes, and with the implication that the primary chondrocytes are contaminated with the fibroblasts.

6-6. Analysis of Methylated CpG Dinucleotide in Promoter Regions of Chondrocyte Marker Genes and MDF Marker Genes The methylation status of the cytosineguanine (CpG) dinucleotide in the promoters of the chondrocyte marker genes (Col2a1 and Acan) and in the promoter of the MDF marker gene (Col1a2) were evaluated for the cloned cells (MK-3, MK-4) and MDFs using bisulfite genomic sequencing analyses. Specifically, bisulfite genomic sequencing analyses were performed using the following technique. A bisulfite treatment was performed using an EpiTect Bisulfite kit (Qiagen) according to the protocol attached to the kit. Table 3 below lists the PCR primers used. The amplification products were cloned into pMD20-T vector using a Mighty TA-cloning Kit (Takara). Ten clones randomly selected for each gene were then sequenced using T7 and T3 primers.

TABLE 3

| Target promoter | Primers used | Sequences |
|---|---|---|
| Col1a2 promoter | Col1a2-Me-S2 | GGATTGGATAGTTTTTGTTTTT |
| | Col1a2-Me-AS2 | AAAACCCAAACCTACCTTATTT |
| Acan promoter | Acan-Me-S2 | GGTGTTAGAGGGGTTTATAGAGTTGAGGA |
| | Acan-Me-AS2 | CTCCTCCAAAAACTTCAATCCTTTATCCCTAC |
| Col2a1 promoter | Col2a1-Me-S3 | TAGAGGGGGTAGTGTGGTAGTT |
| | Col2a1-Me-AS3 | CCCTCATACAAAAAACCCTAAAA |

The results are presented in FIG. 6, e. The cytosineguanine (CpG) dinucleotide in the Col1a2 promoter was highly methylated in MK-3 and MK-4, but was not methylated in MDFs. With regard to the methylation status of the CpG dinucleotide in the Col2a1 and Acan promoters, there was essentially no methylation in both the cloned cells (MK-3, MK-4) and MDFs.

6-7. Analysis of Proliferative Properties

The cloned cells (sixth passage) and MDFs (sixth passage) were cultured in a 10% FBS-containing DMEM medium in a 60-mm dish, and the proliferative properties were evaluated.

Figure 7:
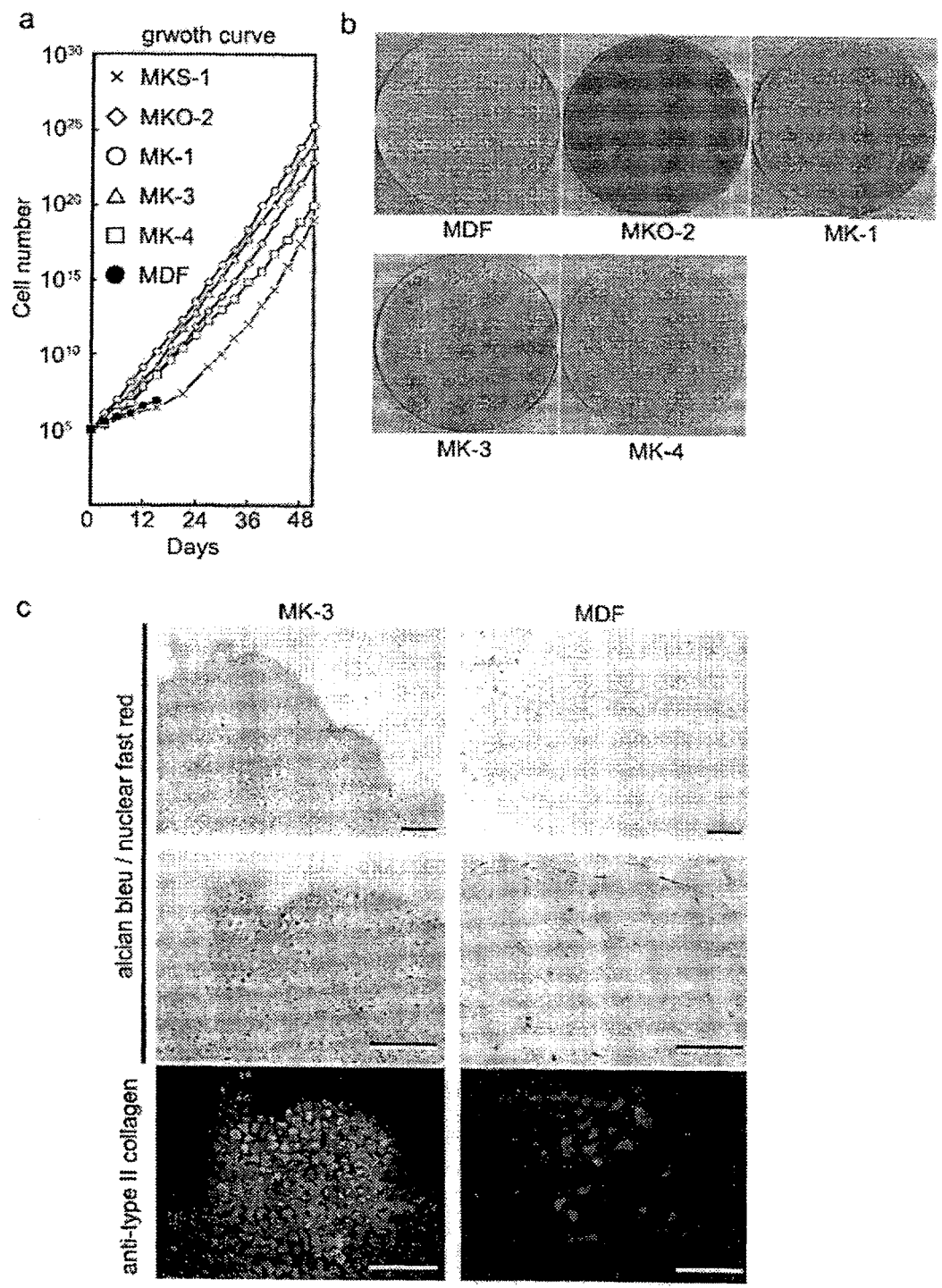
FIG. 7 represents the results of evaluating the properties of the cells (cloned cells) obtained by introducing each factor to MDFs; a, the analysis results for the proliferative properties of MDFs and of the cells obtained by introducing each factor to MDFs; b, the results of alucian blue staining after culturing MDFs and the cells obtained by introducing each factor to MDFs; c, the analysis results for the gel-cell complex formed after culturing MK-3 and MDFs with collagen gels.

The results are presented in FIG. 7, a. MKO-2, MK-1, MK-3, and MK-4 showed exponential growth for at least 48 days, and spindle-shaped or flat cells started to appear after 40 days from the start of culturing. On the other hand, the MDFs stopped growing after 15 days from the start of culturing. MKS-1 showed a rapid increase in growth rate, and underwent a morphological change to a spindle shape after 24 days from the start of culturing. This suggests that MKS-1 dedifferentiation had occurred, and may be a reflection of abnormal chromosome number in the cells.

Some of the cells of each clone were separated after the cell number exceeded $1 \times 10^{10}$ cells, and cultured by being inoculated in a 10-cm dish. The cells were further cultured for days after confluence. The cells were then stained with alucian blue. The results of alucian blue staining are presented in FIG. 7, b. It became clear from the results that the strength of alucian blue staining was stronger in the chondrocyte-like cells than in MDFs, and that the chondrocyte-like cells retained the chondrocyte characteristics even after the cells had reached a certain number.

7. Production of Cartilage Tissue

The cloned cells (MK-3) and MDFs were used to produce cartilage tissue using the following technique.

Collagen gel culture was performed using a collagen gel culture kit (Nitta Gelatin Inc.) according to the protocol attached to the kit. First, the chondrocyte-like cells (MK-3) and MDFs were digested with trypsin/EDTA. The cells were then added to a 0.25% type I acid dissolved collagen solution prepared at 4° C., and suspended in $2 \times 10^7$ cells/ml. The cell suspension (500-μl liquid droplet) was then added to the center of each well of a 6-well plate, and was gelled at 37° C. The resulting gel-cell complex was covered with DMEM medium that contained 10% FBS (3 ml), and cultured under 5% $CO_2$ conditions at 37° C. The medium exchanged with a fresh medium every other day. After being cultured for 3 weeks, the gel-cell complex was fixed with 10% formaldehyde, and embedded in paraffin. A part of the gel-cell complex treated as above was then stained with alucian blue and nuclear fast red. Further, a part of the gel-cell complex was treated with primary antibodies against type II collagen (goat-derived polyclonal antibodies; Santa-Cruz Biotechnology, Inc.; 1:200 dilution), washed, and further treated with secondary antibodies (Alexa Fluor 488 Rabbit Anti-goat IgG; Invitorgen).

The results are presented in FIG. 7, c. Histological analysis of the MK-3 three-dimensional culture product in type I collagen gel confirmed a tissue structure of a small cavity configuration surrounded by substances stained with alucian blue, revealing the formation of a cartilage-like tissue in the gel-cell complex. The MK-3-containing gel-cell complex showed immunoactivity against the anti-type II collagen antibodies, whereas such immunoactivity was not observed in the MDF-containing gel-cell complex.

8. Cartilage Tissue Production In Vivo

Cells of chondrocyte-like morphology (MK-5; chondrocyte-like cells) induced by introducing c-Myc, Klf4, and SOX9 to MDFs were cloned using the foregoing technique. Note that GFP was also introduced to MK-5 using a retro virus vector having incorporated GFP cDNA.

The chondrocyte-like cells (MK-5) were digested with trypsin/EDTA. The cells were then added to a DMEM medium containing 10 volume % FBS, and suspended in $1 \times 10^7$ cells/ml to prepare a cell suspension. The cell suspension (0.1 mL) was subcutaneously injected to the back of a nude mouse (6 weeks of age, female, BALB/cA Jc1-nu/nu).

Figure 8:
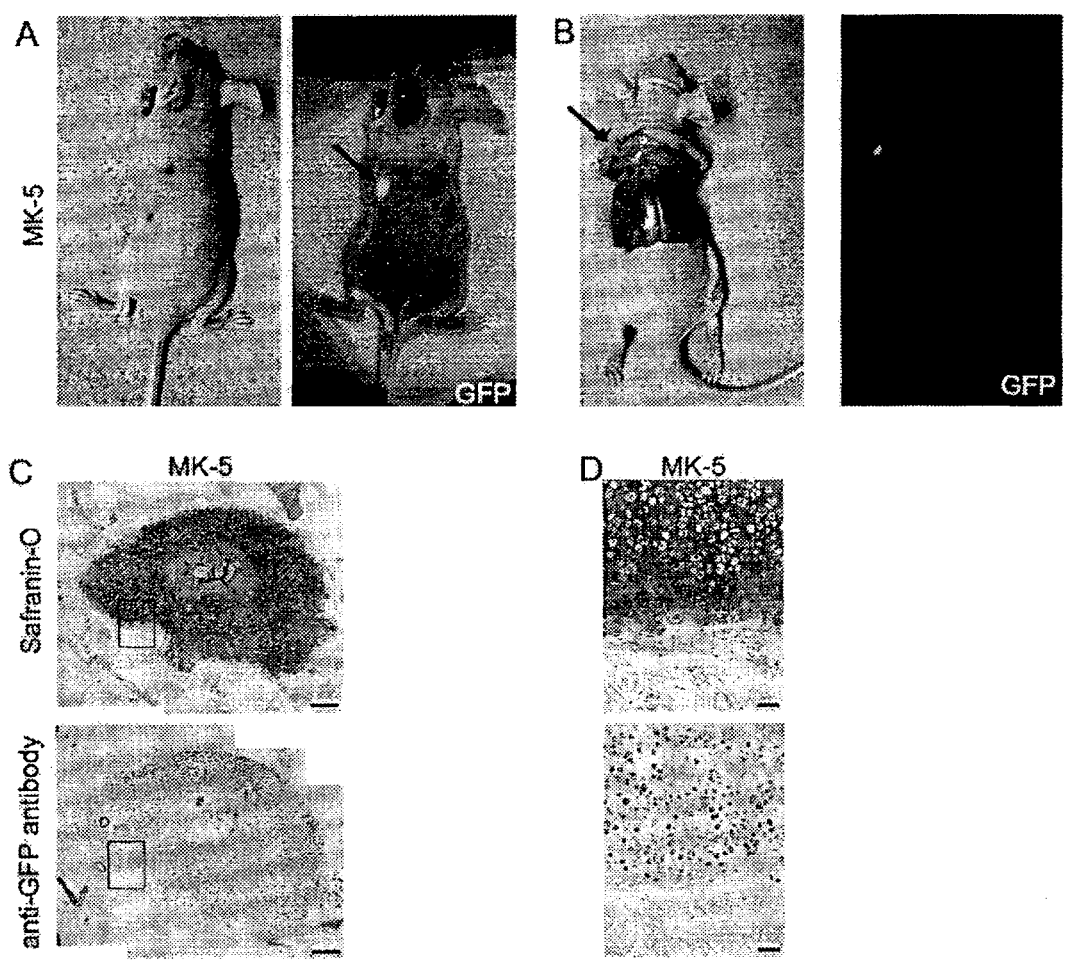
FIG. 8 is a diagram representing nude mice after the subcutaneous injection of cells (MK-5) obtained by introducing c-Myc, Klf-4, Sox9, and GFP to MDFs; A, the result of the observation of the whole nude mouse (right, the result of fluorescence observation); B, the result of the observation of a nude mouse after removing the skin on the back (right, the result of fluorescence observation); C, the result of the safranine O staining of a continuous tissue slice obtained from the subcutaneous site of a cell suspension-injected mouse; D, magnifications of the rectangles shown in C.

The fluorescence at the back of the mouse was observed after 4 weeks from the administration of the cell suspension. GFP-expressing clumps were observed under the skin injected with the MK-5 cell suspension (FIGS. 8, A and B). The cell suspension-injected site was removed, fixed with 4% formaldehyde, and embedded in paraffin. The continuous tissue slice so treated was subjected to safranine O staining, and immunostained with anti-GFP antibodies. The results are presented in FIG. 8, C. The subcutaneous adipose tissue of the MK-5-injected mouse contained tissues of cells scattering in the matrix stained red with safranine O, showing the formation of a cartilage tissue under the skin of the nude mouse. The GFP positive cells are believed to represent the injected chondrocyte-like cells, and the range of these cells completely coincided with the region of the cartilage tissue stained with safranine O. This suggests that all of the survived injected MK-5 cells differentiated into chondrocytes and formed a cartilage tissue. FIG. 8D represents magnifications of the rectangles shown in FIG. 8, C. The result demonstrated that the chondrocyte-like cells were capable of forming a cartilage tissue in the absence of scaffolds, and could be put to practical applications for the regeneration of cartilage tissue.

9. Summary Discussion

It became clear from the foregoing results that the introduction of c-Myc, Klf-4, and Sox9 in combination can produce cells (chondrocyte-like cells) that have a proliferative ability and the properties of the chondrocytes. It was confirmed that the chondrocyte-like cells so produced were actually capable of forming a cartilage tissue of a three-dimensional structure when cultured with a collagen gel, or by being directly administered to an organism.

Example 2

Formation of Cartilage Tissue from Chondrocyte-Like Cells

Methods

Eleven chondrocyte-like cells (MK-5 to MK-15) were obtained by transfecting the MDFs with the c-Myc, Klf4, and Sox9 genes using the method of Example 1. Two of these chondrocyte-like cell lines (MK-7 and MK-10) were digested with trypsin/EDTA, and suspended in a DMEM medium containing 10 volume % FBS to prepare a cell suspension ($1 \times 10^7$ cells/ml). 0.1 ml of the cell suspension was subcutaneously injected to the back of a nude mouse (female, 6 weeks of age, BALB/cA Jcl-nu/nu). The injection site was removed in week 16 post-injection in the MK-7 cell-injected mouse, and in week 8 post-injection in the MK-10 cell-injected mouse. The removed sites were fixed with 4% paraformaldehyde, and embedded in paraffin. Then, tissue slices were produced, and stained with safranine 0, fast green, and iron haematoxylin.

Results

Figure 9:
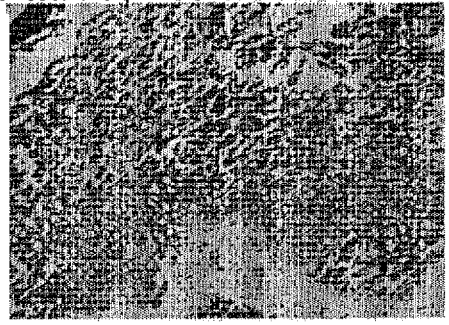
FIG. 9 represents the results of the observation of the tissue at the injection site of a nude mouse after the subcutaneous injection of the cells (chondrocyte-like cells) obtained by introducing c-Myc, Klf-4, and Sox9 to MDFs; A, the results of the safranine O, fast green, and iron haematoxylin staining of the tissue at the injection site after 16 weeks from the injection of the cells (MK-7) obtained by introducing c-Myc, Klf-4, and Sox9 to MDFs; B, the results of the safranine O, fast green, and iron haematoxylin staining of the tissue at the injection site after 8 weeks from the injection of the cells (MK-10) obtained by introducing c-Myc, Klf-4, and Sox9 to MDFs.
Figure 9:
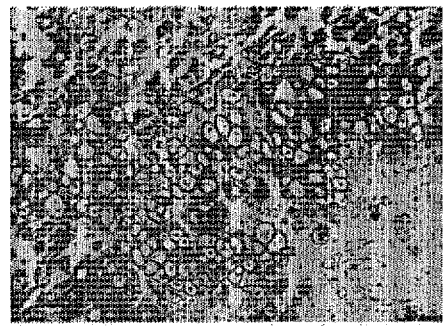
Figure 9:
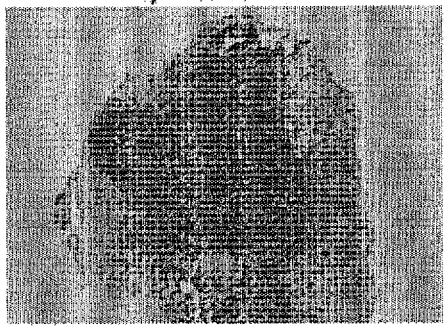
Figure 9:
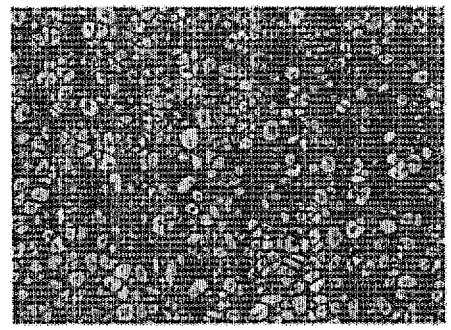

The results are presented in FIG. 9. The subcutaneous adipose tissue of the MK-7 cell- and MK-10 cell-injected mice contained tissues of cells scattering in the matrix stained red with safranine 0, confirming the formation of a cartilage tissue under the skin of the nude mouse. No tumor formation was recognized at the MK-7 cell- or MK-10 cell-injected site.

These results confirmed that the method of the present invention can be used to obtain chondrocyte-like cells without forming tumors for at least 16 weeks.

Example 3

Analysis of Genomic DNA of Chondrocyte-Like Cells

Results

Experiments were conducted to evaluate the identity of the chondrocyte-like cells (MK-1, MK-3, and MK-4) obtained in Example 1, and of the chondrocyte-like cells (MK-5, MK-7, MK-10, and MK-15) obtained in Example 2, as follows.

First, genomic DNA was obtained from the chondrocyte-like cells using an ordinary method, and fragmented by digestion with EcoRI and BamHI. The genomic DNA fragments were developed by electrophoresis on agarose gel, transferred to a nylon membrane, and subjected to southern hybridization using Klf4 cDNA probes.

Figure 10:
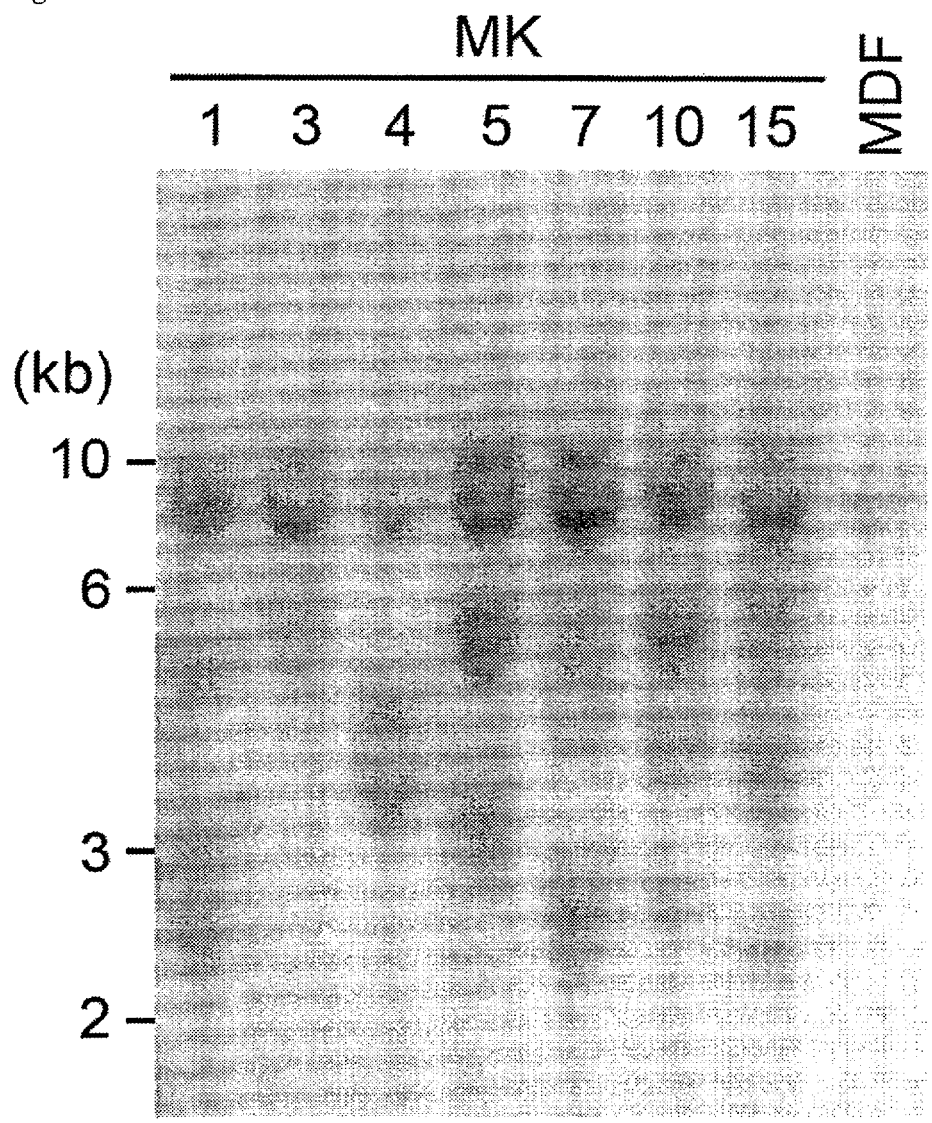
FIG. 10 represents the result of southern hybridization performed for the genomic DNA of each chondrocyte-like cell produced in Examples 1 and 2, using Klf4 cDNA probes.

The results are presented in FIG. 10. As can be seen in FIG. 10, the chondrocyte-like cells obtained in Examples 1 and 2 showed different band patterns for different cell lines, each independently representing an established cell line.

Example 4

Production of Chondrocyte-Like Cells from Adipose tissue-Derived Stromal Cells

Methods

Adipose tissue-derived stromal cells (ADSCs) were separated from the subcutaneous adipose tissue using the method of Reference Literature 5. Specifically, a piece of subcutaneous adipose was removed from a Col11a2-β geo transgenic mouse, 3 to 6 months of age, prepared in the manner described in Example 1. The tissue was sectioned, and treated with 0.2% collagenase at 37° C. for 2 to 4 hours. The liberated cells after the collagenase treatment were filtered through a nylon mesh (pore size, 70 µm; Tokyo Screen, Tokyo, Japan). The separated cells were collected by centrifugation (200×g, 4° C., 10 min). The cells were suspended in a fresh 5% FBS-containing DMEM medium, and centrifuged again (200×g, 4° C., 10 min) to collect cells. The collected cells were cultured in a 60-mm or 100-mm dish to obtain ADSCs (first passage).

Thereafter, c-Myc, Klf-4, and Sox9 were introduced into the subcutaneous adipose cells, and cultured in a 5% FBS-containing DMEM medium containing 500 µg/ml G418 (10 ml), using the method of Example 1.

The cells treated as above were stained with alucian blue and crystal violet, and cell shapes were observed, as in Example 1.

For comparison, a retro virus vector prepared by incorporating GFP cDNA in pMXs vector was used to transform the subcutaneous adipose, and the transformed cells were evaluated, using the technique described above.

Results

Figure 11:
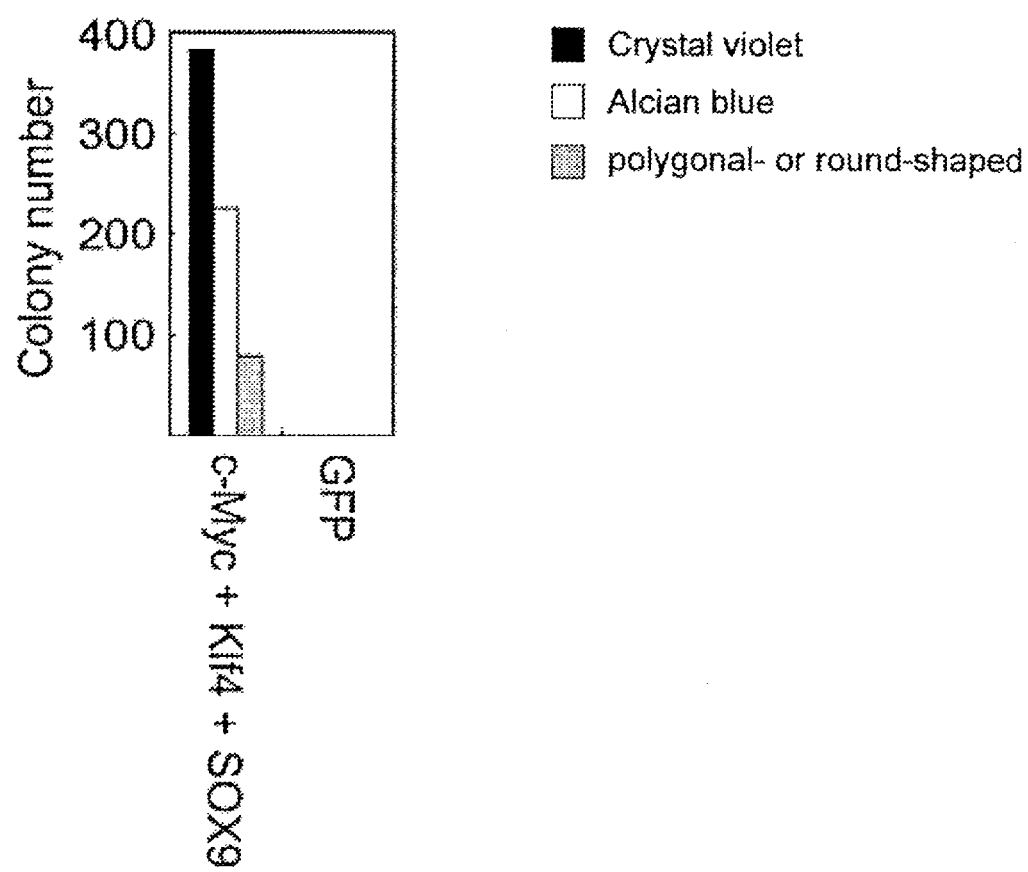
FIG. 11 represents the number of stained colonies counted after the alucian blue staining and crystal violet staining of the colonies obtained by introducing c-Myc, Klf-4, and Sox9 to adipose tissue-derived stromal cells, and the number of colonies formed by polygonal cells.

The results are presented in FIG. 11. Formation of about 380 G418-resistant colonies was observed per 10-cm dish after the introduction of c-Myc, Klf-4, and Sox9 to ADSCs. About 60% of these colonies were stained with alucian blue. Further, about 20% of the stained colonies were round or polygonal cells of chondrocyte-like morphology. No colony formation was recognized in the GFP-introduced adipose-derived stromal cells.

These results strongly suggested that the introduction of c-Myc, Klf-4, and Sox9 to the subcutaneous adipose tissue-derived cells could form chondrocyte-like cells that have a proliferative ability and the properties of the chondrocytes, as with the case of MEFs and MDFs in Example 1.

Example 5

Production of Chondrocyte-Like Cells from Human-Derived Dermal Fibroblasts

Methods
1. Plasmid Preparation

A lentivirus vector system was used to introduce genes to human-derived dermal fibroblasts. LR Clonase II plus reaction (Invitrogen) was used to prepare a human c-MYC-incorporated lentivirus vector (pLe6-CMVp-hc-MYC), a human KLF4-incorporated lentivirus vector (pLe6-CMVp-hKLF4), a human OCT3/4-incorporated lentivirus vector (pLe6-CMVp-hOCT3/4), and a human SOX9-incorporated lentivirus vector (pLe6-CMVp-F(−)hSOX9).
2. Cell Preparation Neonatal normal human dermal fibroblasts (NHDF) were purchased from Lonza (product code: CC-2511). For use, NHDFs were maintained in 10% FBS-containing DMEM medium.
3. Virus Infection 293FT cells ($6 \times 10^6$ cells; Invitrogen) were transfected with 3 µg of each lentivirus vector and 9 µg of Virapower packaging mix (Invitrogen), using Lipofectamine 2000 (Invitrogen). After 48 hours, the transfectant supernatant was collected, and filtered through a 0.45-µm cellulose acetate filter (Whatman). Polybrene (Nacalai Tesque) was then added to the obtained filtrate in a final concentration of 4 mg/ml to prepare a virus solution. A mixed virus solution was prepared by mixing the virus solutions so as to contain equal amounts of Le6-CMVp-hc-MYC, pLe6-CMVp-hKLF4, pLe6-CMVp-hOCT3/4, and pLe6-CMVp-F(−)hSOX9.

A day before the transfection, NHDFs ($5 \times 10^5$ cells) were inoculated in 10% FBS-containing DMEM medium in a 100-mm dish. The medium was removed from the 100-mm dish, and the cells were incubated at 37° C. for 16 hours with addition of the mixed virus solution for transfection with the lentivirus vectors. After being incubated, the cells in the dish were treated with trypsin, and statically cultured in four 10-cm dishes that contained fresh 10% FBS-containing DMEM medium. After the transfection, the cells were statically cultured for 10 days while exchanging the medium with a medium of the same composition every other day. The cultured cells were then stained with alucian blue.

Figure 12:
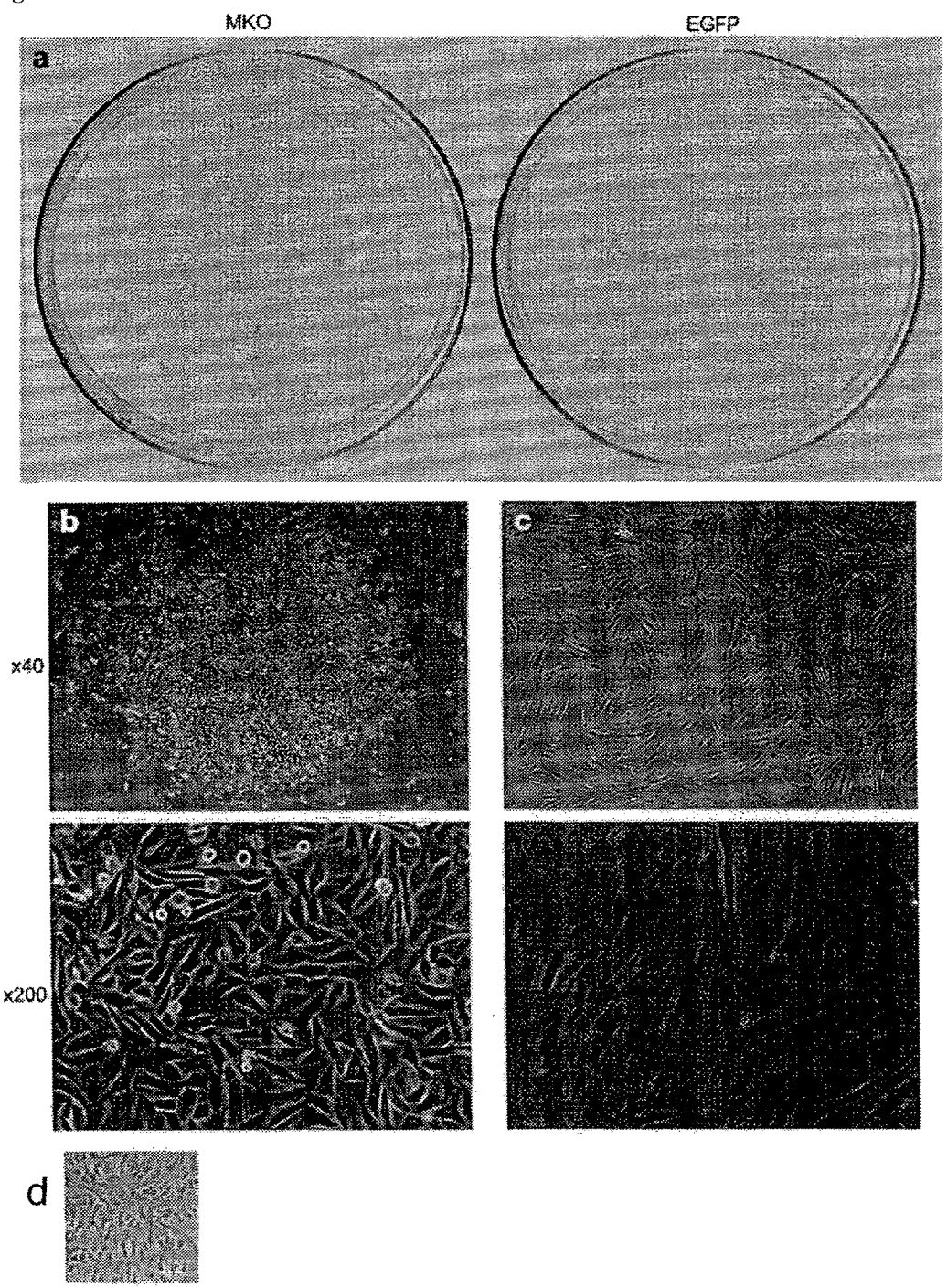
FIG. 12 is a diagram representing the analysis results for the cells obtained by introducing OCT3/4, c-MYC, KLF-4, and SOX9 to NHDFs; a, the results of alucian blue staining for the culture dish (MKO) of OCT3/4-, c-MYC-, KLF-4-, and SOX9-introduced NHDFs, and for the culture dish (EGFP) of EGFP-introduced NHDFs; b, the results of observing the shape of the cells contained in the colonies obtained by introducing OCT3/4, c-MYC, KLF-4, and SOX9 to NHDFs; c, the results of observing the shape of the cells in the culture dish of EGFP-introduced NHDFs; d, a diagram representing the morphology of human primary chondrocytes, copied from the website of Cell Applications, INC. (http://www.cellapplications.com/product_desc.php?id=33&category_id=51&subcategory$_{id}$=68).

For comparison, an EGFP cDNA-incorporated lentivirus vector was used to transform NHDFs, and the transformed cells were evaluated, using the techniques described above.
Results The results are presented in FIG. 12. Cell death was observed in many of the NHDFs to which the three reprogramming factors (OCT3/4, C-MYC, and KLF-4) and SOX9 were introduced. This suggests that the introduction of these reprogramming factors to NHDFs induces cell death in many cells.

The survived cells after the introduction of the three reprogramming factors (OCT3/4, C-MYC, and KLF-4) and SOX9 to NHDFs formed colonies. Some of these colonies were strongly stained with alucian blue. In the culture dish of the EGFP-introduced NHDFs, the cells did not die, and proliferated. The EGFP-introduced NHDFs were not stained with alucian blue (see FIG. 12, *a*). The cells contained in the colonies obtained after culturing with the introduced three reprogramming factors (OCT3/4, C-MYC, and KLF-4) and SOX9 had a morphology (see FIG. 12, *b*) that more resembled the morphology of human primary chondrocytes (see FIG. 12, *d*) than that of the EGFP-introduced cells (see FIG. 12, *c*).

These results strongly suggested that the technique of the present invention can be used to also induce human NHDFs to chondrocyte-like cells that have a proliferative ability and can form a cartilage tissue.

A LIST OF REFERENCE LITERATURES

Reference Literature 1: N. Tsumaki, T. Kimura, Y. Matsui et al., J. Cell Biol. 134 (6), 1573 (1996).

Reference Literature 2: A Nagy, M Gertsenstein, K Vintersten et al., Manipulating the Mouse Embryo., 3rd ed. (Cold Spring Harbor Laboratory Press, New York, 2003).

Reference Literature 3: K. Takahashi and S. Yamanaka, *Cell* 126 (4), 663 (2006).

Reference Literature 4: A. Aszodi, E. B. Hunziker, C. Brakebusch et al., Genes Dev. 17 (19), 2465 (2003).

Reference Literature 5: Bjorntorp, P. et al. Isolation and characterization of cells from rat adipose tissue developing into adipocytes. J. Lipid Res. 19, 316-324 (1978).

SEQUENCE LISTING

PCT chondrocyte-like cells, and _20091218_104843_3.txt

The invention claimed is:

1. A method for producing a cell with at least one chondrocyte property from a somatic cell, comprising the step of transducing a somatic cell with a viral vector from the group consisting of a retroviral vector and an adenoviral vector comprising the following factors:
   a) a SOXgene;
   b) at least one Myc family gene selected from the group consisting of c-Myc, L-Myc and N-Myc; and
   c) at least one Klf family gene selected from the group consisting of Klf4 Klf2 and Klf5, and culturing the transduced cells such that a cell with at least one chondrocyte property is produced.

2. The method according to claim 1, wherein the Myc family gene is a c-Myc gene.

3. The method according to claim 1, wherein the Klf family gene is a Klf4 gene.

4. The method according to claim 1, wherein the somatic cell originates in humans.

5. The method according to claim 1, wherein the somatic cell is a dermal fibroblast or an adipose tissue-derived stromal cell.

6. The method of claim 1, wherein a SOX9 gene, a c-Myc gene, and a Klf4 gene are the only factors introduced into the somatic cell.

* * * * *

```
SEQUENCE LISTING

<160> NUMBER OF SEQ ID NOS: 42

<210> SEQ ID NO 1
<211> LENGTH: 18
<212> TYPE: DNA
<213> ORGANISM: Artificial
<220> FEATURE:
<223> OTHER INFORMATION: A primer for LacZ gene

<400> SEQUENCE: 1
cgctaccatt accagttg                                                 18

<210> SEQ ID NO 2
<211> LENGTH: 18
<212> TYPE: DNA
<213> ORGANISM: Artificial
<220> FEATURE:
<223> OTHER INFORMATION: A primer for neomycine-resistant gene

<400> SEQUENCE: 2
ccagtcatag ccgaatag                                                 18

<210> SEQ ID NO 3
<211> LENGTH: 19
<212> TYPE: DNA
<213> ORGANISM: Artificial
<220> FEATURE:
<223> OTHER INFORMATION: A primer for Klf4 Tg RT S

<400> SEQUENCE: 3
gaccaccttg ccttacaca                                                19

<210> SEQ ID NO 4
<211> LENGTH: 21
<212> TYPE: DNA
<213> ORGANISM: Artificial
<220> FEATURE:
<223> OTHER INFORMATION: A primer for Klf4 Tg RT AS

<400> SEQUENCE: 4 cccttttct ggagactaaa t                                              21

<210> SEQ ID NO 5
<211> LENGTH: 19
```

```
<212> TYPE: DNA
<213> ORGANISM: Artificial
<220> FEATURE:
<223> OTHER INFORMATION: A primer for c-myc Tg RT S

<400> SEQUENCE: 5
tcgctaccat taccagttg                                             19

<210> SEQ ID NO 6
<211> LENGTH: 21
<212> TYPE: DNA
<213> ORGANISM: Artificial
<220> FEATURE:
<223> OTHER INFORMATION: A primer for c-myc Tg RT AS

<400> SEQUENCE: 6
ccctttttct ggagactaaa t                                          21

<210> SEQ ID NO 7
<211> LENGTH: 18
<212> TYPE: DNA
<213> ORGANISM: Artificial
<220> FEATURE:
<223> OTHER INFORMATION: A primer for Oct3/4 Tg RT S

<400> SEQUENCE: 7
tcccatgcat tcaaactg                                              18

<210> SEQ ID NO 8
<211> LENGTH: 20
<212> TYPE: DNA
<213> ORGANISM: Artificial
<220> FEATURE:
<223> OTHER INFORMATION: A primer for Oct3/4 Tg RT AS

<400> SEQUENCE: 8
cccctgttgt gcttttaatc                                            20

<210> SEQ ID NO 9
<211> LENGTH: 18
<212> TYPE: DNA
<213> ORGANISM: Artificial
<220> FEATURE:
<223> OTHER INFORMATION: A primer for Sox2 Tg RT S

<400> SEQUENCE: 9
ccattaacgg cacactgc                                              18

<210> SEQ ID NO 10
<211> LENGTH: 18
<212> TYPE: DNA
<213> ORGANISM: Artificial
<220> FEATURE:
<223> OTHER INFORMATION: A primer for Sox2 Tg RT AS

<400> SEQUENCE: 10
ccttacgcga aatacggg                                              18

<210> SEQ ID NO 11
<211> LENGTH: 18
<212> TYPE: DNA
<213> ORGANISM: Artificial
<220> FEATURE:
<223> OTHER INFORMATION: A primer for SOX9 RT S

<400> SEQUENCE: 11
```
ccagcgaacg cacatcaa                                              18

<210> SEQ ID NO 12
<211> LENGTH: 21
<212> TYPE: DNA
<213> ORGANISM: Artificial
<220> FEATURE:
<223> OTHER INFORMATION: A primer for SOX9 RT AS

<400> SEQUENCE: 12
ggagttctgg tggtcggtgt a                                          21

<210> SEQ ID NO 13
<211> LENGTH: 21
<212> TYPE: DNA
<213> ORGANISM: Artificial
<220> FEATURE:
<223> OTHER INFORMATION: A primer for Gapdh RT S

<400> SEQUENCE: 13
gagatgatga ccctttggc t                                           21

<210> SEQ ID NO 14
<211> LENGTH: 20
<212> TYPE: DNA
<213> ORGANISM: Artificial
<220> FEATURE:
<223> OTHER INFORMATION: A primer for Gapdh RT AS

<400> SEQUENCE: 14
tcaaggccga gaatgggaag                                            20

<210> SEQ ID NO 15
<211> LENGTH: 18
<212> TYPE: DNA
<213> ORGANISM: Artificial
<220> FEATURE:
<223> OTHER INFORMATION: A primer for Sox5 RT S

<400> SEQUENCE: 15
cccctcaaag cctctgtc                                              18

<210> SEQ ID NO 16
<211> LENGTH: 18
<212> TYPE: DNA
<213> ORGANISM: Artificial
<220> FEATURE:
<223> OTHER INFORMATION: A primer for Sox5 RT AS

<400> SEQUENCE: 16
cttgctgctc tcgcctga                                              18

<210> SEQ ID NO 17
<211> LENGTH: 18
<212> TYPE: DNA
<213> ORGANISM: Artificial
<220> FEATURE:
<223> OTHER INFORMATION: A primer for Sox6 RT S

<400> SEQUENCE: 17
tcatcccggc ctaagaca                                              18

<210> SEQ ID NO 18
<211> LENGTH: 19
<212> TYPE: DNA
<213> ORGANISM: Artificial

```
<220> FEATURE:
<223> OTHER INFORMATION: A primer for Sox6 RT AS

<400> SEQUENCE: 18
acagggcagg agagttgag                                                19

<210> SEQ ID NO 19
<211> LENGTH: 21
<212> TYPE: DNA
<213> ORGANISM: Artificial
<220> FEATURE:
<223> OTHER INFORMATION: A primer for Col2a1 RT S

<400> SEQUENCE: 19
ttgagacagc acgacgtgga g                                             21

<210> SEQ ID NO 20
<211> LENGTH: 21
<212> TYPE: DNA
<213> ORGANISM: Artificial
<220> FEATURE:
<223> OTHER INFORMATION: A primer for Col2a1 RT AS

<400> SEQUENCE: 20
agccaggttg ccatcgccat a                                             21

<210> SEQ ID NO 21
<211> LENGTH: 20
<212> TYPE: DNA
<213> ORGANISM: Artificial
<220> FEATURE:
<223> OTHER INFORMATION: A primer for Col11a1 RT S

<400> SEQUENCE: 21
atgagtatgc acctgaggat                                               20

<210> SEQ ID NO 22
<211> LENGTH: 22
<212> TYPE: DNA
<213> ORGANISM: Artificial
<220> FEATURE:
<223> OTHER INFORMATION: A primer for Col11a1 RT AS

<400> SEQUENCE: 22
ggagtctcag tctggtaagg tt                                            22

<210> SEQ ID NO 23
<211> LENGTH: 21
<212> TYPE: DNA
<213> ORGANISM: Artificial
<220> FEATURE:
<223> OTHER INFORMATION: A primer for Col11a2 RT S

<400> SEQUENCE: 23
gactgtaaga agcgagttac c                                             21

<210> SEQ ID NO 24
<211> LENGTH: 19
<212> TYPE: DNA
<213> ORGANISM: Artificial
<220> FEATURE:
<223> OTHER INFORMATION: A primer for Col11a2 RT AS

<400> SEQUENCE: 24
gccttcaaag acttcatcg                                                19
```

```
<210> SEQ ID NO 25
<211> LENGTH: 21
<212> TYPE: DNA
<213> ORGANISM: Artificial
<220> FEATURE:
<223> OTHER INFORMATION: A primer for Col9a1 RT S

<400> SEQUENCE: 25
tgtagacttc aggattccaa c                                              21

<210> SEQ ID NO 26
<211> LENGTH: 18
<212> TYPE: DNA
<213> ORGANISM: Artificial
<220> FEATURE:
<223> OTHER INFORMATION: A primer for Col9a1 RT AS

<400> SEQUENCE: 26
ccaaatgttc cagtgctt                                                  18

<210> SEQ ID NO 27
<211> LENGTH: 18
<212> TYPE: DNA
<213> ORGANISM: Artificial
<220> FEATURE:
<223> OTHER INFORMATION: A primer for Col9a2 RT S

<400> SEQUENCE: 27
tggaagggag tgcggatt                                                  18

<210> SEQ ID NO 28
<211> LENGTH: 20
<212> TYPE: DNA
<213> ORGANISM: Artificial
<220> FEATURE:
<223> OTHER INFORMATION: A primer for Col9a2 RT AS

<400> SEQUENCE: 28
cgaccaggat cacccagaat                                                20

<210> SEQ ID NO 29
<211> LENGTH: 19
<212> TYPE: DNA
<213> ORGANISM: Artificial
<220> FEATURE:
<223> OTHER INFORMATION: A primer for Col9a3 RT S

<400> SEQUENCE: 29
tggtgtgccg ggacttgat                                                 19

<210> SEQ ID NO 30
<211> LENGTH: 20
<212> TYPE: DNA
<213> ORGANISM: Artificial
<220> FEATURE:
<223> OTHER INFORMATION: A primer for Col9a3 RT AS

<400> SEQUENCE: 30
cacccagctc gccagttcta                                                20

<210> SEQ ID NO 31
<211> LENGTH: 20
<212> TYPE: DNA
<213> ORGANISM: Artificial
<220> FEATURE:
<223> OTHER INFORMATION: A primer for Col1a1 RT S
```

```
<400> SEQUENCE: 31
gcaacagtcg cttcacctac                                          20

<210> SEQ ID NO 32
<211> LENGTH: 19
<212> TYPE: DNA
<213> ORGANISM: Artificial
<220> FEATURE:
<223> OTHER INFORMATION: A primer for Col1a1 RT AS

<400> SEQUENCE: 32
gtgggaggga accagattg                                           19

<210> SEQ ID NO 33
<211> LENGTH: 21
<212> TYPE: DNA
<213> ORGANISM: Artificial
<220> FEATURE:
<223> OTHER INFORMATION: A primer for Col1a2 RT S

<400> SEQUENCE: 33
tcgggcctgc tggtgttcgt g                                        21

<210> SEQ ID NO 34
<211> LENGTH: 24
<212> TYPE: DNA
<213> ORGANISM: Artificial
<220> FEATURE:
<223> OTHER INFORMATION: A primer for Col1a2 RT AS

<400> SEQUENCE: 34
tgggcgcggc tgtatgagtt cttc                                     24

<210> SEQ ID NO 35
<211> LENGTH: 20
<212> TYPE: DNA
<213> ORGANISM: Artificial
<220> FEATURE:
<223> OTHER INFORMATION: A primer for Acan RT S

<400> SEQUENCE: 35
ccctcgggca gaagaaagat                                          20

<210> SEQ ID NO 36
<211> LENGTH: 21
<212> TYPE: DNA
<213> ORGANISM: Artificial
<220> FEATURE:
<223> OTHER INFORMATION: A primer for Acan RT AS

<400> SEQUENCE: 36
cgcttctgta gcctgtgctt g                                        21

<210> SEQ ID NO 37
<211> LENGTH: 22
<212> TYPE: DNA
<213> ORGANISM: Artificial
<220> FEATURE:
<223> OTHER INFORMATION: A primer for Cola2-Me-S2

<400> SEQUENCE: 37
ggattggata gttttgtttt tt                                       22

<210> SEQ ID NO 38
```

```
<211> LENGTH: 22
<212> TYPE: DNA
<213> ORGANISM: Artificial
<220> FEATURE:
<223> OTHER INFORMATION: primer for Cola2-Me-AS2

<400> SEQUENCE: 38
aaaacccaaa cctaccttat tt                                              22

<210> SEQ ID NO 39
<211> LENGTH: 29
<212> TYPE: DNA
<213> ORGANISM: Artificial
<220> FEATURE:
<223> OTHER INFORMATION: primer for Acan-Me-S2

<400> SEQUENCE: 39
ggtgttagag gggtttatag agttgagga                                       29

<210> SEQ ID NO 40
<211> LENGTH: 32
<212> TYPE: DNA
<213> ORGANISM: Artificial
<220> FEATURE:
<223> OTHER INFORMATION: A primer for Acan-Me-AS2

<400> SEQUENCE: 40
ctcctccaaa aacttcaatc ctttatccct ac                                   32

<210> SEQ ID NO 41
<211> LENGTH: 22
<212> TYPE: DNA
<213> ORGANISM: Artificial
<220> FEATURE:
<223> OTHER INFORMATION: A primer for Col2a1-Me-S2

<400> SEQUENCE: 41
tagagggggt agtgtggtag tt                                              22

<210> SEQ ID NO 42
<211> LENGTH: 23
<212> TYPE: DNA
<213> ORGANISM: Artificial
<220> FEATURE:
<223> OTHER INFORMATION: A primer for Col2a1-Me-AS2

<400> SEQUENCE: 42
ccctcataca aaaaccccta aaa                                             23
```